(12) United States Patent
Stoner et al.

(10) Patent No.: US 10,890,581 B2
(45) Date of Patent: Jan. 12, 2021

(54) SUBSTRATE-MEDIATED REACTORS FOR BIOASSAYS

(71) Applicant: FIREFLY BIOWORKS, INC., Cambridge, MA (US)

(72) Inventors: Isaac Stoner, Cambridge, MA (US); Timothy Erps, Salem, MA (US); Daniel Pregibon, Somerville, MA (US); Jessica Dawn Tytell, Cambridge, MA (US); Andreas Windemuth, Belmont, MA (US); Graeme Doran, Cambridge, MA (US)

(73) Assignee: FIREFLY BIOWORKS, INC., Cambridge, MA (US)

( * ) Notice: Subject to any disclaimer, the term of this patent is extended or adjusted under 35 U.S.C. 154(b) by 506 days.

(21) Appl. No.: 15/313,366

(22) PCT Filed: May 22, 2015

(86) PCT No.: PCT/US2015/032319
§ 371 (c)(1),
(2) Date: Nov. 22, 2016

(87) PCT Pub. No.: WO2015/179848
PCT Pub. Date: Nov. 26, 2015

(65) Prior Publication Data
US 2018/0052154 A1 Feb. 22, 2018

Related U.S. Application Data

(60) Provisional application No. 62/002,664, filed on May 23, 2014.

(51) Int. Cl.
*G01N 33/543* (2006.01)
*G01N 33/538* (2006.01)

(52) U.S. Cl.
CPC ....... *G01N 33/538* (2013.01); *G01N 33/5432* (2013.01); *G01N 33/5436* (2013.01)

(58) Field of Classification Search
None
See application file for complete search history.

(56) References Cited

U.S. PATENT DOCUMENTS

| 7,947,487 B2 | 5/2011 | Doyle et al. |
| 2010/0172898 A1 | 7/2010 | Doyle et al. |

(Continued)

FOREIGN PATENT DOCUMENTS

| WO | 2011/156432 A2 | 12/2011 |
| WO | 2011/156434 | 12/2011 |

OTHER PUBLICATIONS

Jang et al., "Multiplexed enzyme-based bioassay within microfluidic devices using shape-coded hydrogel microparticles", Sensors and Actuators B: Chemical, 143(2): 681-688, (Nov. 8, 2009).

(Continued)

*Primary Examiner* — Rebecca M Giere
(74) *Attorney, Agent, or Firm* — Proskauer Rose LLP; Fangli Chen

(57) ABSTRACT

The present invention provides, among other things, methods, compositions and systems for highly efficient, robust, multiplex analysis of biomolecules based on substrate-mediated compartmentalization in conjunction with controlled release of assay reagents for interference-free detection of biomolecules.

19 Claims, 9 Drawing Sheets

A. Bead in a droplet

B. Substrate-defined droplet

C. Substrate-defined multi-droplet structure

D. Nested Substrates

(56) References Cited

U.S. PATENT DOCUMENTS

2013/0210653 A1  8/2013  Pregibon et al.
2013/0244909 A1  9/2013  Windemuth et al.

OTHER PUBLICATIONS

Ju et al., "Fluorescence energy transfer dye-labeled primers for DNA sequencing and analysis", Proc. Nat'l Acad. Sci. (USA) 92: 4347 (1995).

Sakai-Kato et al., "Integration of biomolecules into analytical systems by means of silica sol-gel technology", Analytical sciences: the international journal of the Japan Society for Analytical Chemistry, Japan, p. 969 (Aug. 1, 2009).

Stears et al., "A novel, sensitive detection system for high-density microarrays using dendrimer technology", Physiol Genomics, 3:93-99 (2000).

Tsagkogeorgas et al., "Encapsulation of biomolecules for bioanalytical purposes: Preparation of diclofenac antibody-doped nanometer-sized silica particles by reverse micelle and sol-gel processing", Analytica Chimica Acta, vols. 573-574, pp. 133-137, (Jul. 28, 2006).

Zhu et al., "High-Sensitivity Capillary Electrophoresis of Double-Stranded DNA Fragments Using Monomeric and Dimeric Fluorescent Intercalating Dyes", Anal. Chem. 66:1941-1948 (1994).

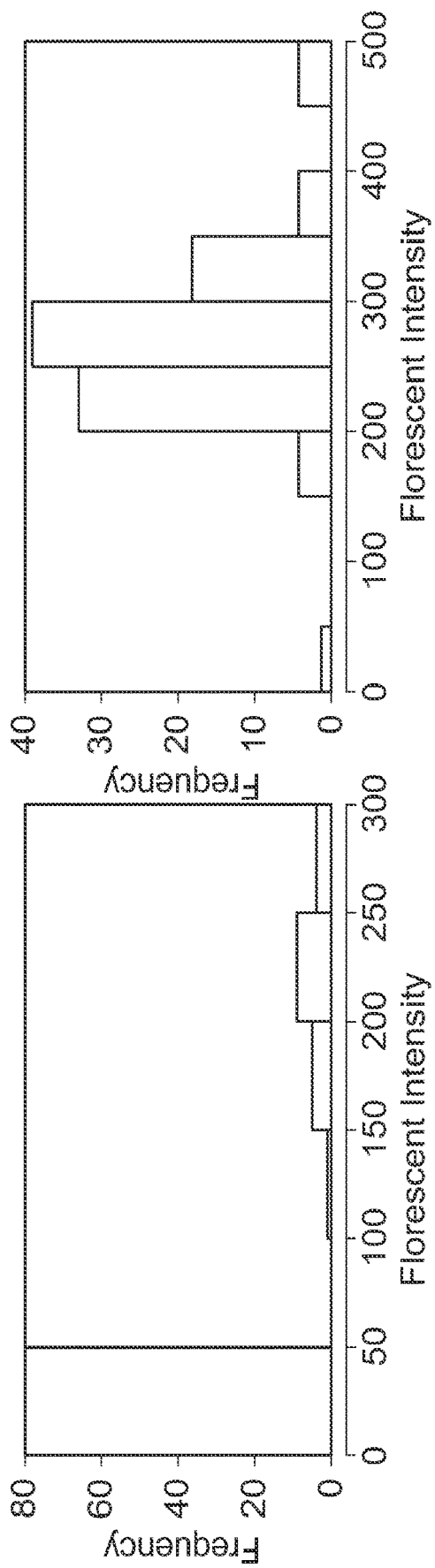
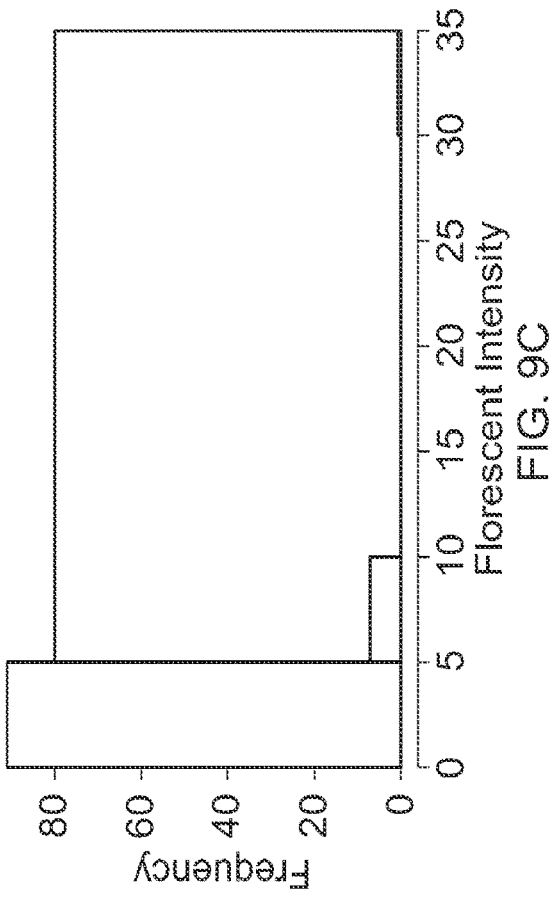
FIG. 9A
FIG. 9B
FIG. 9C

SUBSTRATE-MEDIATED REACTORS FOR BIOASSAYS

RELATED APPLICATIONS

This application claims priority to and the benefit of U.S. Provisional Patent Application Ser. No. 62/002,664, filed May 23, 2014, the entire contents of which are herein incorporated by reference.

BACKGROUND

The quantification of biomolecules is fundamental to basic science, translational research, and clinical diagnostics. Methods that enable the simultaneous analysis of multiple biomarkers simplify workflow and minimize sample volume requirements. However, it is often difficult to quantify biomarkers in a multiplexed manner due to the unintended interaction of target-specific detection reagents. These "off-target" interactions limit the multiplexing level, sensitivity, and specificity of biomolecule measurement across protein and nucleic acid targets.

The multiplexed detection of proteins is an exceptionally challenging task given the inherent promiscuity of antibodies. One method used commonly for immunoassays is a sandwich assay. In this assay, targets are captured using a substrate-bound "capture antibody" and the binding of target is made apparent by the use of a "detection antibody" that binds the target and carries a detectable moiety.

Because antibodies always exhibit some level of cross-reactivity with off-target sample molecules or off-target detection antibodies, the performance of assays is often compromised when immunoassays are performed in a multiplexed format. As a result, sandwich assays are used most frequently in an enzyme-linked immunosorbant assay (ELISA) format, where a single protein target is detected per assay well. The development of multiplexed protein assays using antibody pairs that perform well in single-plex ELISAs still requires significant validation efforts to assure compatibility.

Similar compatibility challenges exist in the multiplexed detection of nucleic acids. One example of this is in multiplexed PCR. While PCR provides a robust means of amplifying target molecules for highly-sensitive detection, the technique is prone to non-specific amplification when amplifying multiple nucleic acid targets at once. Typically, the amplification of each target is performed using a primer set with forward and reverse primers both specific to that target. When amplifying multiple targets in a single well, multiple primer sets are used. Similar to the cross-reactivity of antibodies in immunoassays, primers may also interact with each other (heterodimers), with off-target strands, or with themselves (homodimers), leading to the unintentional amplification of off-target species. For this reason, most PCR reactions, especially in the case of quantitative PCR, are physically isolated in individual reaction wells.

SUMMARY

The present invention provides a highly efficient, robust, and multiplexed assay system for target-specific detection of biomolecules. In particular, the invention is based on substrate-mediated compartmentalization in conjunction with controlled release of assay reagents for interference-free detection of biomolecules using a simple instrument, such as, flow cytometer or microarray scanner. Thus, the present invention overcomes various challenges associated with reagent incompatibility and "off-target" interactions and achieves significantly improved multiplexing level, sensitivity, and specificity of biomolecule measurement across protein and nucleic acid targets.

Thus, in one aspect, the present invention provides methods for analyzing biomolecules, comprising: incubating a sample with a plurality of multifunctional substrates, wherein each multifunctional substrate comprises a target capture region bearing one or more capture moieties, each of which specifically binds a target biomolecule, and a reagent storage region bearing one or more detection reagents through a releasable means, under conditions that permit binding between the target biomolecule and the capture moieties; contacting an immiscible fluid with the plurality of multifunctional substrates in a carrier fluid, thereby forming a plurality of compartments, each comprising an individual multifunctional substrate; releasing the one or more detection reagents from the reagent storage region such that the detection reagents bind to the target biomolecule bound to the capture moieties within an individual compartment; and analyzing the binding between the detection moieties and the biomolecule bound to the capture moieties, thereby analyzing the presence or amount of the target biomolecule in the sample.

In some embodiments, the multifunctional substrates are multifunctional microparticles. In some embodiments, the substrates are made of hydrogel. In some embodiments, the hydrogel is selected from photoresist, silica, polystyrene, polyethylene glycol, polyethylene glycol methacrylate, agarose, chitosan, alginate, PLGA, or any combination thereof. In some embodiments, the microparticles are non-spherical particles. In some embodiments, the shape of each compartment is substantially defined by the shape of the multifunctional substrate.

In some embodiments, the plurality of multifunctional substrates comprise monodisperse microparticles. In some embodiments, the plurality of multifunctional substrates comprise polydisperse microparticles between 1 µm and 500 µm in their longest dimension. In some embodiments, the multifunctional substrates comprise a cavity, depression, or hole.

In some embodiments, the multifunctional substrates comprise one or more cells or bacteria. In some embodiments, the one or more cells or bacteria release molecules that are capable of diffusing through the carrier fluid within individual compartments. In some embodiments, the one or more cells or bacteria release molecules that are capable of diffusing through an impermeable or semipermeable immiscible phase. In some embodiments, the molecules released by the one or more cells or bacteria have therapeutic or probiotic activity.

In some embodiments, the one or more capture moieties are selected from antibodies, nanobodies, oligonucleotide probes, peptide nucleic acids, small molecules, aptamers, cells, bacteria, viruses, organelles, peptides, or combination thereof. In some embodiments, the one or more detection reagents are selected from detection antibodies, nanobodies, enzymes, PCR primers, proteins, oligonucleotides, peptides, aptamers, small molecules, other chemical compounds, or combination thereof. In some embodiments, the one or more detection reagents are labeled with a detection moiety selected from fluorophores, chromophores, radioisotopes, biotin, enzyme products, antibodies, quantum dots, molecular beacons, and/or aptamers.

In some embodiments, the multifunctional substrates comprise one or more hydrophobic regions. In some embodiments, the one or more hydrophobic regions is comprised of a hydrophobic polymer.

In some embodiments, the immiscible fluid is selectively permeable. In some embodiments, the immiscible fluid is an oil and the carrier fluid is an aqueous fluid. In some embodiments, the immiscible fluid is an aqueous fluid and the carrier fluid is an oil. In some embodiments, the oil is selected from Fluorinert FC-40 oil, Tegasoft, or mineral oil. In some embodiments, the oil further comprises a surfactant such as ABIL WE-09, PFPE-PEG, or some other bi-functional molecule.

In some embodiments, the target biomolecule is a protein, a nucleic acid, a cell, a bacteria, or a chemical compound.

In some embodiments, the releasable means are selected from reversible interactions, an irreversible reaction, reversible crosslinkers, or photocleavable linkers. In some embodiments, the reversible interactions are selected from electrostatic interactions, physical interactions, magnetic interactions, chemical interactions, or nucleic acid duplex formation. In some embodiments, the irreversible reaction is bond cleavage. In some embodiments, the reversible crosslinkers are selected from EGS, DSP, and/or DST that is cleavable by hydroxylamine, thiols, and/or periodate, respectively. In some embodiments, the photocleavable linkers are 1-(2-nitropheny)ethyl based linkers.

In some embodiments, the one or more detection reagents are released from the reagent storage region into the compartment in a controlled manner. In some embodiments, the controlled manner comprises using heat, ultraviolet light, visible light, microwave radiation, enzymatic catalysis, pH, or a specific chemical agent as a stimulus. In some embodiments, the one or more detection reagents are released at different times.

In some embodiments, the contacting step comprises a step of emulsification. In some embodiments, the step of emulsification is accomplished via mechanical agitation or shearing, acoustic agitation, or a microfluidic device.

In some embodiments, the analyzing step comprises quantifying the amount of detection moiety present in the target capture region, thereby determining the amount of target biomolecule in the sample.

In some embodiments, the each multifunctional substrate further comprises an encoding region.

In some embodiments, the multifunctional substrates are analyzed with a flow cytometer or microarray scanner based on a fluorescent or visible identifier.

In some embodiments, the compartments are reversed prior to detection.

In some embodiments, the plurality of multifunctional substrates comprise multiple subsets of multifunctional substrates bearing multiple capture moieties against multiple target biomolecules, and wherein the method analyzes the presence or amount of the multiple target biomolecules in the sample.

In another aspect, the present invention provides methods for producing substrate-defined compartments comprising: contacting an immiscible fluid with a collection of substrates dispersed in a carrier fluid to form a mixture; and adding energy to the mixture, thereby creating discrete, substrate-containing compartments of carrier fluid within the immiscible fluid, wherein the size of the compartments is larger than the size of compartments formed in the absence of substrate.

In some embodiments, the substrate is a particle. In some embodiments, the substrate is made of hydrogel. In some embodiments, the particle is non-spherical. In some embodiments, the shape of the compartments is substantially defined by the shape of the particle contained therein.

In some embodiments, the substrates include monodisperse particles or polydisperse particles between 1 μm and 500 μm in their longest dimension.

In some embodiments, the substrates comprise a cavity, depression, or hole.

In some embodiments, the hydrogel is selected from photoresist, silica, polystyrene, polyethylene glycol, polyethylene glycol methacrylate, agarose, chitosan, alginate, PLGA, or a combination thereof.

In some embodiments, the substrate contains two or more distinct regions. In some embodiments, each distinct region contains covalently bound biological probes, reversibly bound detection reagents, small molecules, reactive molecules, cells, bacteria, and/or combination thereof.

In some embodiments, the substrates comprise one or more hydrophobic regions. In some embodiments, the one or more hydrophobic regions are comprised of a hydrophobic polymer.

In some embodiments, the immiscible fluid is an oil and the carrier fluid is an aqueous fluid. In some embodiments, the immiscible fluid is an aqueous fluid and the carrier fluid is an oil.

In another aspect, the present invention provides multifunctional substrates (e.g., particles), comprising: at least one target capture region, at least one reagent storage region and at least one encoding region, wherein the target capture region bears one or more antibodies, nanobodies, oligonucleotide probes, peptide nucleic acids, small molecules, aptamers, cells, bacteria, viruses, organelles, peptides, or combination thereof; wherein the reagent storage region bears one or more releasable detection agents, and wherein the encoding region comprises identification features.

In some embodiments, the one or more detection reagents are selected from detection antibodies, nanobodies, enzymes, PCR primers, proteins, oligonucleotides, peptides, aptamers, small molecules, other chemical compounds, or combination thereof. In some embodiments, the multifunctional particle further comprises one or more hydrophobic regions. In some embodiments, the multifunctional particle comprises a cavity, depression, or hole.

Other features, objects, and advantages of the present invention are apparent in the detailed description, drawings and claims that follow. It should be understood, however, that the detailed description, the drawings, and the claims, while indicating embodiments of the present invention, are given by way of illustration only, not limitation. Various changes and modifications within the scope of the invention will become apparent to those skilled in the art.

BRIEF DESCRIPTION OF THE DRAWING

The drawings are for illustration purposes only, not for limitation.

FIG. 9 comprised of panels A, B and C shows exemplary histograms of the particle fluorescent intensity resulting from particle encapsulation, as well as the appropriate positive and negative controls.

DEFINITIONS

Figure 1:
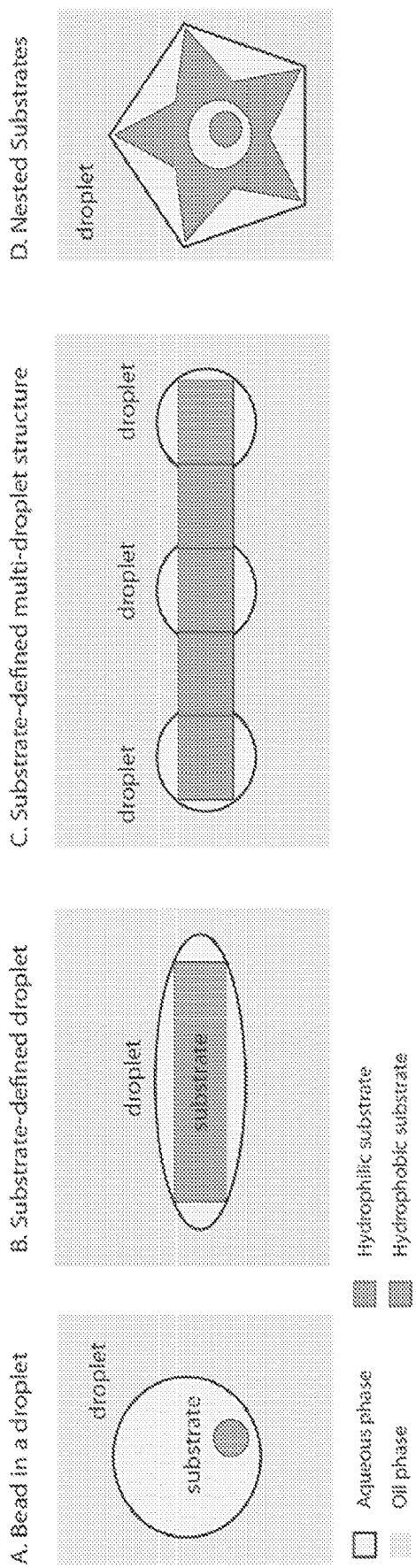
FIG. 1 shows exemplary modes of droplet-contained substrates in multiphase systems. Shown is a bead encapsulated in a much larger droplet (left), a larger substrate that defines the droplet (middle left), a multi-functional substrate that defines multiple aqueous compartments (middle right), and a nested substrate system (right).

In order for the present invention to be more readily understood, certain terms are first defined. Additional definitions for the following terms and other terms are set forth throughout the specification.

Analyte: As used herein, the term "analyte" broadly refers to any substance to be analyzed, detected, measured, or quantified. Examples of analytes include, but are not limited to, proteins, peptides, hormones, haptens, antigens, antibodies, receptors, enzymes, nucleic acids, and combinations thereof. In some embodiments, the term "analyte" is used interchangeably with the term "target biomolecule".

Associated: As used herein, the terms "associated", "conjugated", "linked", "attached", "complexed", and "tethered," and grammatical equivalents, typically refer to two or more moieties connected with one another, either directly or indirectly (e.g., via one or more additional moieties that serve as a linking agent), to form a structure that is sufficiently stable so that the moieties remain connected under the conditions in which the structure is used, e.g., physiological conditions. In some embodiments, the moieties are attached to one another by one or more covalent bonds. In some embodiments, the moieties are attached to one another by a mechanism that involves specific (but non-covalent) binding (e.g. streptavidin/avidin interactions, antibody/antigen interactions, etc.). Alternatively or additionally, a sufficient number of weaker interactions (non-covalent) can provide sufficient stability for moieties to remain connected. Exemplary non-covalent interactions include, but are not limited to, affinity interactions, metal coordination, physical adsorption, host-guest interactions, hydrophobic interactions, pi stacking interactions, hydrogen bonding interactions, van der Waals interactions, magnetic interactions, electrostatic interactions, dipole-dipole interactions, etc.

Biomolecules: The term "biomolecules", as used herein, refers to molecules (e.g., proteins, amino acids, peptides, polynucleotides, nucleotides, carbohydrates, sugars, lipids, nucleoproteins, glycoproteins, lipoproteins, steroids, etc.) whether naturally-occurring or artificially created (e.g., by synthetic or recombinant methods) that are commonly found in cells and tissues. Specific classes of biomolecules include, but are not limited to, enzymes, receptors, neurotransmitters, hormones, cytokines, cell response modifiers such as growth factors and chemotactic factors, antibodies, vaccines, haptens, toxins, interferons, ribozymes, anti-sense agents, plasmids, DNA, and RNA.

Complement: As used herein, the terms "complement," "complementary" and "complementarity," refer to the pairing of nucleotide sequences according to Watson/Crick pairing rules. For example, a sequence 5'-GCGGTCCCA-3' has the complementary sequence of 5'-TGGGACCGC-3'. A complement sequence can also be a sequence of RNA complementary to the DNA sequence. Certain bases not commonly found in natural nucleic acids may be included in the complementary nucleic acids including, but not limited to, inosine, 7-deazaguanine, Locked Nucleic Acids (LNA), and Peptide Nucleic Acids (PNA). Complementary need not be perfect; stable duplexes may contain mismatched base pairs, degenerative, or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs.

Crude: As used herein, the term "crude," when used in connection with a biological sample, refers to a sample which is in a substantially unrefined state. For example, a crude sample can be cell lysates or biopsy tissue sample. A crude sample may exist in solution or as a dry preparation.

Encoding region, coding region, or barcoded region: As used herein, the terms "encoding region," "coding region," "barcoded region", or grammatical equivalents, refer to a region on an object or substrate (e.g., particle) that can be used to identify the object or substrate (e.g., particle). These terms may be used inter-changeably. Typically, an encoding region of an object bears graphical and/or optical features associated with the identity of the object. Such graphical and/or optical features are also referred to as signature features of the object. In some embodiments, an encoding region of an object bears spatially patterned features (e.g., stripes with various shapes and/or dimensions, or a series of holes with various sizes) that give rise to variable fluorescent intensities (of one or multiple wavelengths). In some embodiments, an encoding region of an object bears various type and/or amount of fluorophores or other detectable moieties, in various spatial patterns, that give rise to variable fluorescent signals (e.g., different colors and/or intensities) in various patterns.

Functionalization: As used herein, the term "functionalization" refers to any process of modifying a material by bringing physical, chemical or biological characteristics different from the ones originally found on the material. Typically, functionalization involves introducing functional groups to the material. As used herein, functional groups are specific groups of atoms within molecules that are responsible for the characteristic chemical reactions of those molecules. As used herein, functional groups include both chemical (e.g., ester, carboxylate, alkyl) and biological groups (e.g., oligonucleotide adapter, or linker sequences).

Hybridize: As used herein, the term "hybridize" or "hybridization" refers to a process where two complementary nucleic acid strands anneal to each other under appropriately stringent conditions. Oligonucleotides or probes suitable for hybridizations typically contain 10-100 nucleotides in length (e.g., 18-50, 12-70, 10-30, 10-24, 18-36 nucleotides in length). Nucleic acid hybridization techniques are well known in the art. See, e.g., Sambrook, et al., 1989, Molecular Cloning: A Laboratory Manual, Second Edition, Cold Spring Harbor Press, Plainview, N.Y. Those skilled in the art understand how to estimate and adjust the stringency of hybridization conditions such that sequences having at least a desired level of complementary will stably hybridize, while those having lower complementary will not. For examples of hybridization conditions and parameters, see, e.g., Sambrook, et al., 1989, Molecular Cloning: A Laboratory Manual, Second Edition, Cold Spring Harbor Press, Plainview, N.Y.; Ausubel, F. M. et al. 1994, Current Protocols in Molecular Biology. John Wiley & Sons, Secaucus, N.J.

Labeled: The terms "labeled" and "labeled with a detectable agent or moiety" are used herein interchangeably to specify that an entity (e.g., a nucleic acid probe, antibody, etc.) can be visualized, for example following binding to another entity (e.g., a nucleic acid, polypeptide, etc.). The detectable agent or moiety may be selected such that it generates a signal which can be measured and whose intensity is related to (e.g., proportional to) the amount of bound entity. A wide variety of systems for labeling and/or detecting proteins and peptides are known in the art. Labeled proteins and peptides can be prepared by incorporation of, or conjugation to, a label that is detectable by spectroscopic, photochemical, biochemical, immunochemical, electrical, optical, chemical or other means. A label or labeling moiety may be directly detectable (i.e., it does not require any further reaction or manipulation to be detectable, e.g., a fluorophore is directly detectable) or it may be indirectly detectable (i.e., it is made detectable through reaction or binding with another entity that is detectable, e.g., a hapten is detectable by immunostaining after reaction with an appropriate antibody comprising a reporter such as a fluorophore). Suitable detectable agents include, but are not limited to, radionucleotides, fluorophores, chemiluminescent agents, microparticles, enzymes, colorimetric labels, magnetic labels, haptens, molecular beacons, aptamer beacons, and the like.

Monodisperse or polydisperse: As used herein, the terms "monodisperse" or "monosized" refer to a collection of objects that have substantially the same size and shape when in the context of particles, and substantially the same mass in the context of polymers. Conversely, a collection of objects that have an inconsistent size, shape and mass distribution are called polydisperse. Monodisperse particles are typically synthesized through the use of template-based synthesis.

Particle: The term "particle," as used herein, refers to a discrete object. Such object can be of any shape or size. Composition of particles may vary, depending on applications and methods of synthesis. Suitable materials include, but are not limited to, plastics, ceramics, glass, polystyrene, methylstyrene, acrylic polymers, metal, paramagnetic materials, thoria sol, carbon graphited, titanium dioxide, latex or cross-linked dextrans such as Sepharose, cellulose, nylon, cross-linked micelles and teflon. In some embodiments, particles can be optically or magnetically detectable. In some embodiments, particles contain fluorescent or luminescent moieties, or other detectable moieties. In some embodiments, particles having a diameter or otherwise their longest dimension of less than 1000 micrometers (um) are also referred to as microparticles. In some embodiments, particles having a diameter of less than 1000 nanometers (nm) are also referred to as nanoparticles.

Polynucleotide, nucleic acid, or oligonucleotide: The terms "polynucleotide", "nucleic acid", or "oligonucleotide" refer to a polymer of nucleotides. The terms "polynucleotide", "nucleic acid", and "oligonucleotide", may be used interchangeably. Typically, a polynucleotide comprises at least three nucleotides. DNAs and RNAs are polynucleotides. The polymer may include natural nucleosides (i.e., adenosine, thymidine, guanosine, cytidine, uridine, deoxyadenosine, deoxythymidine, deoxyguanosine, and deoxycytidine), nucleoside analogs (e.g., 2-aminoadenosine, 2-thiothymidine, inosine, pyrrolopyrimidine, 3-methyl adenosine, C5-propynylcytidine, C5-propynyluridine, C5-bromouridine, C5-fluorouridine, C5-iodouridine, C5-methylcytidine, 7-deazaadenosine, 7-deazaguanosine, 8-oxoadenosine, 8-oxoguanosine, O(6)-methylguanine, and 2-thiocytidine), chemically modified bases, biologically modified bases (e.g., methylated bases), intercalated bases, modified sugars (e.g., 2'-fluororibose, ribose, 2'-deoxyribose, arabinose, and hexose), or modified phosphate groups (e.g., phosphorothioates and 5'-N-phosphoramidite linkages).

Object or substrate: As used herein, the terms "object" and "substrate" are used interchangeably and refer to any discrete mass. An object or substrate can be a particle, bead, planar surface, phage, macromolecules, cell, micro-organism, and the like.

Probe: As used herein, the term "probe" refers to a fragment of DNA or RNA of variable length (e.g., 3-1000 bases long), which is used to detect the presence of target nucleotide sequences that are complementary to the sequence in the probe. Typically, the probe hybridizes to single-stranded nucleic acid (DNA or RNA) whose base sequence allows probe-target base pairing due to complementarity between the probe and target.

Signal: As used herein, the term "signal" refers to a detectable and/or measurable entity. In certain embodiments, the signal is detectable by the human eye, e.g., visible. For example, the signal could be or could relate to intensity and/or wavelength of color in the visible spectrum. Non-limiting examples of such signals include colored precipitates and colored soluble products resulting from a chemical reaction such as an enzymatic reaction. In certain embodiments, the signal is detectable using an apparatus. In some embodiments, the signal is generated from a fluorophore that emits fluorescent light when excited, where the light is detectable with a fluorescence detector. In some embodiments, the signal is or relates to light (e.g., visible light and/or ultraviolet light) that is detectable by a spectrophotometer. For example, light generated by a chemiluminescent reaction could be used as a signal. In some embodiments, the signal is or relates to radiation, e.g., radiation emitted by radioisotopes, infrared radiation, etc. In certain embodiments, the signal is a direct or indirect indicator of a property of a physical entity. For example, a signal could be used as an indicator of amount and/or concentration of a nucleic acid in a biological sample and/or in a reaction vessel.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

DETAILED DESCRIPTION

The present invention provides, among other things, methods, compositions and systems for highly efficient, robust, multiplex analysis of biomolecules based on substrate-mediated compartmentalization in conjunction with controlled release of assay reagents for interference-free detection of biomolecules. In some embodiments, a suitable system for the present invention is a particle-defined microemulsion system.

Various aspects of the invention are described in detail in the following sections. The use of sections is not meant to limit the invention. Each section can apply to any aspect of the invention. In this application, the use of "or" mean "and/or" unless stated otherwise.

Multi-phase System Encapsulation

According to the present invention, substrate-mediated compartmentalization may take place in a multi-phase system. In a multi-phase system, the formation of droplets of a discontinuous fluid in a continuous fluid is typically determined by the physical characteristics of the system. In particular, the surface energy (related to the densities, viscosities, and surface tensions of the fluids) and kinetic energy (related to fluid velocities) of the system are important. Given specific surface and kinetic energies in a system, phase separation occurs to provide droplets of a characteristic size that can be predicted using the Weber Number (We=$\rho v^2 l/\sigma$) where, $\rho$, v, l, and $\sigma$ represent fluid density, velocity, droplet diameter, and surface tension, respectively.

In the case of droplet-confined beads, the solid beads used are usually significantly smaller than the droplets formed in the system in order to allow for a solution-based reaction. When substrates significantly smaller than the characteristic droplet size are present in the discontinuous phase, the mechanism of droplet formation is not greatly affected. However, when substrates significantly larger than the characteristic droplet size are present, the physics of droplet formation are altered dramatically, and droplet formation is largely substrate-mediated. FIG. 1 shows several modes of this substrate encapsulation in multi-phase systems. The substrates used in this process can cover a wide size range, typically from about 1 µm to 1000 µm (e.g., about 1 µm to 900 µm, about 1 µm to 800 µm, about 1 µm to 700 µm, about 1 µm to 600 µm, from 1 µm to 500 µm, from 1 µm to 400 µm, from 1 µm to 300 µm, from 1 µm to 200 µm, or from 1 µm to 100 µm). Substrates may be hydrophilic, hydrophobic, or a combination of both (Bong, Pregibon, & Doyle, 2009; Dendukuri, Hatton, & Doyle, 2007).

Various methods of encapsulation can be used, one such being a water-in-oil emulsion which utilizes substrates (e.g., hydrogel substrates) to define aqueous droplets within a continuous immiscible phase. Alternatively, reversible sol-gel polymers can be used to selectively separate hydrogel-templated aqueous compartments within a less-hydrated gel phase, effectively eliminating or reducing diffusion between compartments. An additional method of isolating hydrogel reactors could include crosslinking an impermeable polymer shell around each microparticle, encapsulating hydrogel substrates and isolating each aqueous compartment.

As used herein, "carrier fluid" is used to describe the medium in which substrates are suspended and which is encapsulated with the substrates. "Immiscible fluid" is used herein to describe any medium (i.e., liquid) that is incapable of mixing with a carrier fluid. Typically, an immiscible fluid surrounds the encapsulated substrates. In some embodiments, an immiscible fluid comprises an oil and a carrier fluid comprises an aqueous fluid. In some embodiments, an immiscible fluid comprises an aqueous fluid and a carrier fluid comprises an oil. In some embodiments, a suitable oil is Fluorinert FC-40 oil, Tegasoft, or mineral oil. In some embodiments, a suitable oil may further contain a surfactant such as ABIL WE-09, PFPE-PEG, or some other bi-functional molecule. In some embodiments, a discontinuous phase is any medium encapsulated within a compartment and a continuous phase is any medium surrounding the encapsulated compartments.

In some embodiments, the immiscible fluid is selectively permeable. A phase may be selectively permeable if some compounds may travel from the continuous phase into the discontinuous phase, but other compounds cannot travel from the discontinuous phase out to the continuous phase. In some embodiments, the selective permeability is based on size. In some embodiments, the selective permeability is based on a property other than size. In some embodiments, a compound can travel from the continuous phase to the discontinuous phase because it is soluble in both the continuous phase and in the discontinuous phase.

Various methods can also be used to break emulsions. These methods include: gravity settling, centrifugation, electrical coalescence, and chemical methods (e.g. adding electrolytes to neutralize the charge of the droplets' interfaces, thereby causing coalescence).

Multifunctional Substrates

Substrates or objects (e.g., particles) suitable for the present invention may comprise one or multiple functional regions. Suitable substrates or objects may have a planer, spherical or non-spherical morphologies. Suitable substrates or objects may be solid, semi-solid, polymer, or the like. Exemplary suitable substrate may be made of a material selected from the group consisting of hydrogel, glass, photoresists, silica, polystyrene, polyethylene glycol, agarose, chitosan, alginate, PLGA, optical fiber, cellulose, and combination thereof. In some embodiments, suitable material is hydrogel. Suitable substrates may also be in various form, size and shape. For example, a suitable substrate may be a patterned planar substrate, microchips, plastics, beads, biofilms, or particles. In some embodiments, a suitable substrate is a particle. For illustration purposes, particles are described in detail below.

Particles

Particles suitable for use in accordance with the present invention can be made of any material. Suitable particles can be biocompatible or non-biocompatible. Suitable particles can also be biodegradable or non-biodegradable.

In some embodiments, particles are hydrogels. In general, hydrogels comprise a substantially dilute crosslinked network. Water or other fluids can penetrate the network, forming such a hydrogel. In some embodiments, hydrogels suitable for use in the present invention are made of or comprise a hydrophilic polymer. For example, hydrophilic polymers may comprise anionic groups (e.g. phosphate group, sulphate group, carboxylate group); cationic groups (e.g. quaternary amine group); or polar groups (e.g. hydroxyl group, thiol group, amine group). In some embodiments, hydrogels are superabsorbent (e.g. they can contain over 99% water) and possess a degree of flexibility very similar to natural tissue, due to their significant water content. Both of weight and volume, hydrogels are fluid in composition and thus exhibit densities similar to those of their constituent liquids (e.g., water). The present invention encompasses the recognition that hydrogels are particularly useful in some embodiments of the present invention. In some embodiments, hydrogel is used to define aqueous compartments within a continuous hydrophobic phase that is immiscible or partially miscible with aqueous or hydrophilic solution. Without wishing to be bound to any particular theory, it is contemplated that hydrogels enable 1) ease of implementation with detection instruments, in particular, commercially available instruments without substantial modifications (e.g., flow cytometers), and 2) ease of incorporation of functional moieties (e.g., in a single lithography-polymerization step) without requiring surface functionalization.

Various additional materials and methods can be used to synthesize particles. In some embodiments, particles may be made of or comprise one or more polymers. Polymers used in particles may be natural polymers or unnatural (e.g. synthetic) polymers. In some embodiments, polymers can be linear or branched polymers. In some embodiments, polymers can be dendrimers. Polymers may be homopolymers or copolymers comprising two or more monomers. In terms of sequence, copolymers may be block copolymers, graft copolymers, random copolymers, blends, mixtures, and/or adducts of any of the foregoing and other polymers.

In some embodiments, particles of the present invention may be made of or comprise a natural polymer, such as a carbohydrate, protein, nucleic acid, lipid, etc. In some embodiments, natural polymers may be synthetically manufactured. Many natural polymers, such as collagen, hyaluronic acid (HA), and fibrin, which derived from various components of the mammalian extracellular matrix can be used in particles of the present invention. Collagen is one of the main proteins of the mammalian extracellular matrix, while HA is a polysaccharide that is found in nearly all animal tissues. Alginate and agarose are polysaccharides that are derived from marine algae sources. Some advantages of natural polymers include low toxicity and high biocompatibility.

In some embodiments, including in some preferred embodiments, each substrate is composed of a hydrated, interpenetrating polymer network, containing as much as 99.9% water by volume. Each substrate can be functionalized with specific capture moieties, such as oligonucleotide probes, antibodies, aptamers, small molecules, cells, or peptides. These capture moieties can be used to specifically bind analytes from biological samples including isolated DNA or RNA, cell lysates, tissue digest, or plasma/serum. Additionally, these hydrogel substrates can be functionalized in a reversible or irreversible manner with one or multiple detection reagents, such as an analyte-specific detection antibodies or PCR primers.

Size and Shape

In general, particles suitable for the present invention can be of any size. In some embodiments, suitable particles have a size greater than 1 µm up to about 1000 µm in at least one dimension (e.g., 1-500 µm, 1-450 µm, 1-400 µm, 1-350 µm, 1-300 µm, 1-250 µm, 1-200 µm, 1-150 µm, 1-100 µm, 1-50 µm, 2-50 µm, 2-100 µm, 50-1000 µm, 50-500 µm, 50-450 µm, 50-400 µm, 50-350 µm, 50-300 µm, 50-250 µm, 50-200 µm, 50-150 µm, 100-1000 µm, 100-500 µm, 100-450 µm, 100-400 µm, 100-350 µm, 100-300 µm, 100-250 µm, 100-200 µm, 100-150 µm in at least one dimension). In some embodiments, the volume defined by particles suitable for the present invention is on the order of picoliters (e.g., the volume of the particle and/or the particle-defined compartment can be 1-1,000, 1-900, 1-800, 1-700, 1-600, 1-500, 1-400, 1-300, 1-200, or 1-100 picoliters). In some embodiments, the volume defined by particles suitable for the present invention is on the order of femtoliters (e.g., the volume of the particle and/or the particle-defined compartment can be 1-1,000, 1-900, 1-800, 1-700, 1-600, 1-500, 1-400, 1-300, 1-200, or 1-100 femtoliters).

Particles may have various aspect ratios of their dimensions, such as length/width, length/thickness, etc. Particles, in some embodiments, can have at least one dimension, such as length, that is longer than another dimension, such as width. According to the present invention, particles having at least one aspect ratio greater than one may be particularly useful in flowthrough scanning (e.g., in a flow cytometer) to facilitate their self-alignment. In some embodiments, particles may have at least one aspect ratio of at least about 1.5:1, at least about 2:1, at least about 2.5:1, at least about 3:1, at least about 4:1, at least about 5:1, at least about 10:1, at least about 15:1, or even greater.

Suitable particles can have a variety of different shapes including, but not limited to, spheres, oblate spheroids, cylinders, ovals, ellipses, shells, cubes, cuboids, cones, pyramids, rods (e.g., cylinders or elongated structures having a square or rectangular cross-section), tetrapods (particles having four leg-like appendages), triangles, prisms, etc. In some embodiments, particles are rod-shaped. In some embodiments, particles are bar-shaped. In some embodiments, particles are bead-shaped. In some embodiments, particles are column-shaped. In some embodiments, particles are ribbon or chain-like. In some embodiments, particles can be of any geometry or symmetry. For example, planar, circular, rounded, tubular, ring-shaped, tetrahedral, hexagonal, octagonal particles, particles of other regular geometries, and/or particles of irregular geometries can also be used in the present invention. In some embodiments, the substrate comprises a cavity, depression, or hole. In some embodiments, the presence of a cavity, depression or hole allows more space for reactions to occur within a compartment.

In some embodiments, the substrates comprise one or more hydrophobic regions. In some embodiments, the one or more hydrophobic regions comprise a hydrophobic polymer. In some embodiments, the hydrophobic polymer comprises a highly cross-linked polymer network. In some embodiments, the hydrophobic polymer comprises a hydrophobic polymer precursor. In some embodiments, the substrates comprise a plurality of compartments surrounding each substrate, wherein the compartments are separated by hydrophobic regions of the substrate. In some embodiments, the substrates comprising one or more hydrophobic regions are multifunctional.

Suitable particles can be monodisperse in that each particle in the population is the same size and shape. Suitable particles can be polydisperse in that the population of particles comprises particles of different sizes and shapes.

Target Capture Region

In some embodiments, particles suitable for the present invention comprise one or more target capture regions. Various capture moieties or groups may be introduced to the surface of the substrates that produce selected functionality (e.g., to capture target biomolecules). Such capture moieties can be chemically attached to the surface, e.g., by covalent incorporation, or can be physically attached thereto or entrapped therein. Desired capture moieties specific for target biomolecules may be designed using various methods known in the art. In some embodiments, desired capture moieties include antibodies, nanobodies, oligonucleotide probes, peptide nucleic acids, small molecules, aptamers, cells, bacteria, viruses, organelles, peptides, or combination thereof.

Reagent Storage Region

In some embodiments, particles suitable for the present invention comprise one or more reagent storage regions. Various detection reagents may be introduced to the surface of the substrates that produce selected functionality. Such detection reagents can attached to the substrates via releasable means. In some embodiments, the releasable means are selected from reversible interactions, an irreversible reaction, reversible crosslinkers, or photocleavable linkers. In some embodiments, the reversible interactions are selected from electrostatic interactions, physical interactions, magnetic interactions, or nucleic acid duplex formation. In some embodiments, the irreversible reaction is bond cleavage. In some embodiments, the reversible crosslinkers are selected from EGS, DSP, and/or DST that is cleavable by hydroxylamine, thiols, and/or periodate, respectively. In some embodiments, wherein the photocleavable linkers are 1-(2-nitropheny)ethyl based linkers. Desired detection reagents specific for target biomolecules may be designed using various methods known in the art. In some embodiments, desired detection reagents include detection antibodies, nanobodies, enzymes, PCR primers, proteins, oligonucleotides, peptides, aptamers, small molecules, other chemical compounds, or combination thereof.

Encoding Region

In some embodiments, a suitable particle comprises one or more coding regions (also referred to as encoding regions) bearing detectable moieties that give the identity of the probes attached to or embedded in the one or more probe regions of the same particle. Various detectable moieties may be used including fluorophores, chromophores, radioisotopes, quantum dots, nanoparticles and/or intercalating DNA/RNA dyes. Additional examples of detectable moieties are described in the Detectable Entities section below.

In some embodiments, the one or more coding regions bear fluorophores such that the level of fluorescence is used for encoding. For example, fluorescence in each coding region can be distinguishable at multiple levels, e.g., up to 10-20 levels (e.g., up to 1, 2, 3, 4, 5, 6, 7, 8, 9, 10, 11, 12, 13, 14, 15, 16, 17, 18, 19, or 20 levels). As a non-limiting example, when three coding regions are used and 10 levels are distinguishable for each, it would allow up to 1000 (10×10×10) unique codes. Additionally or alternatively, multiple signals (e.g., different fluorescent colors) can be used for encoding. In some embodiments, each coding region has one signal distinct from each other. This may be accomplished by using blends of various fluorophores, with unique emission spectra.

In some embodiments, target capture regions, reagent storage regions and encoding regions are separated from one another by inert regions. In some embodiments, one or more target capture regions and one or more encoding regions overlap with each other. In some embodiments, an encoding and target capture region can be the same region.

Bioassays

Once substrates have been effectively isolated from each other by compartmentalization, detection reagents stored within the substrate can be released into the defined aqueous compartments for binding, amplification, or detection. By combining controlled release with substrate-mediated compartmentalization, it is possible to perform multiplexed target capture in bulk, with release and binding of detection reagents in isolation.

In general, the controlled release of reagents can be accomplished using reversible interactions (e.g., electrostatic, physical, magnetic, etc.) that can be modulated using an external stimulus, or irreversible reactions (bond cleavage, etc.). Detection reagents can be attached by reversible crosslinkers such as EGS, DSP, and/or DST that can be cleaved by hydroxylamine, thiols, and periodate respectively. In a similar method, photocleavable linkers such as 1-(2-nitrophenyl)ethyl based linkers can be used to selectively release detection moieties when exposed to ultraviolet light.

Figure 2:
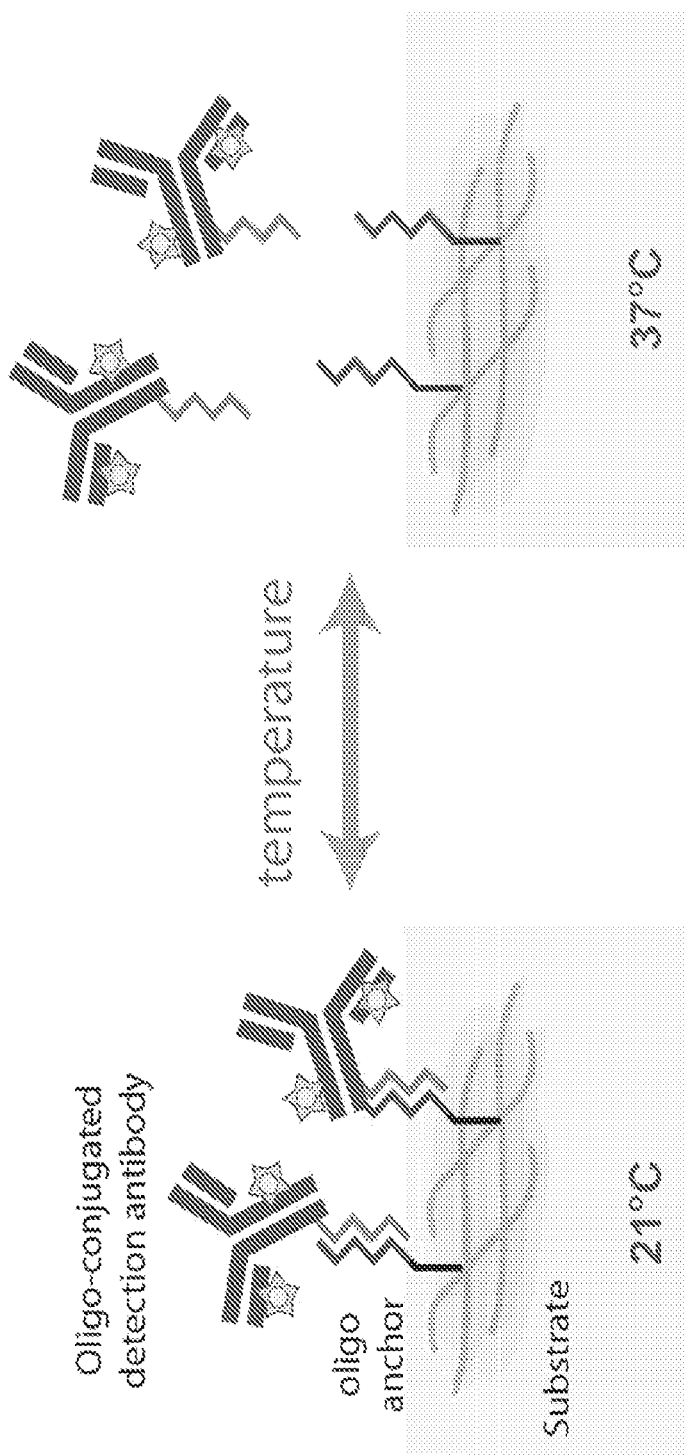
FIG. 2 shows an exemplary reversible release and capture of oligo-conjugated detection antibody using changes in temperature.

An effective method of reversibly storing the detection reagent within the hydrogel matrix is through DNA duplex formation. The detection reagent, functionalized with a known oligonucleotide sequence, can be hybridized to the complementary "anchor" sequence which is covalently attached within the hydrogel matrix. This allows for controlled release of the reagent at the appropriate temperature or buffer condition. For example, one can use DNA hybridization to an oligo-decorated substrate with temperature as a stimulus for reagent release and recapture as shown in FIG. 2.

This method of combining substrate-mediated compartmentalization with controlled release of reagents within the compartments allows for incompatible monoclonal or polyclonal antibodies or PCR primers to be used in parallel, each contained in separate substrate-defined compartments. When the encapsulated detection reaction is complete, the reaction encapsulation can be reversed, allowing for additional assay processing or analysis. Reversing the water-in-oil emulsion can be accomplished by adding the appropriate breaking reagent, typically a solvent that selectively alters the surfactant conditions in the continuous oil phase.

The methods of substrate-mediated compartmentalization and controlled reagent release can be utilized for the separation, manipulation, amplification, quantification, or isolation of analytes, reagents, structures, or cells. Substrates may bear one or more multiple functional regions for target capture, reagent storage, and/or substrate identification. In addition, the substrate may bear multiple chemistries to facilitate droplet formation, interfacial alignment, or sub-compartmentalization.

In some embodiments, the bioassay performed within each compartment is an immunoassay. In some embodiments, the immunoassay is an enzyme-linked immunosorbent assay (ELISA). In some embodiments, the ELISA is a sandwich ELISA. In some embodiments, the bioassay performed within each compartment is polymerase chain reaction (PCR). In some embodiments, the PCR is highly multiplexed PCR. In some embodiments, the bioassay performed within each compartment is single cell analysis. In some embodiments, the bioassay performed within each compartment is digital PCR. In some embodiments, the bioassay performed within each compartment is cell secretion analysis. In some embodiments, the bioassay performed within each compartment is multiplexed ChIP-Seq (combination of chromatin immunoprecipitation with massively parallel DNA sequencing).

Target Analytes

Methods and compositions described herein may be used to analyze any target biomolecule. In general, target biomolecules may be any form of polypeptides, proteins, oligopeptides, amino acids, polysaccharides, oligosaccharides, monosaccharides, polynucleotides, nucleic acids, oligonucleotides, nucleotides, nucleosides, metabolites, lipids, fatty acids, glycolipids, sterols, glycerolipids, vitamins, hormones, neurotransmitters, or any combination thereof present in a sample. A target nucleic acid, in various embodiments, can be one that is found in a biological organism including, for example, a microorganism or infectious agent, or any naturally occurring, bioengineered or synthesized component thereof. In certain embodiments of the present invention, a target nucleic acid may be or contain a portion of a gene, a regulatory sequence, genomic DNA, cDNA, RNA including mRNA, rRNA, microRNA, small interfering RNA (siRNA), long noncoding RNA (lnc RNA), small nuclear RNA (snRNA), double stranded RNA (ds RNA) or any combination thereof. In certain embodiments of the present invention, a target nucleic acid may be a nucleic acid analogue or artificial nucleic acid, such as DNA/RNA chimeras.

Samples

Any of a variety of samples may be suitable for use with methods disclosed herein including, but not limited to biological samples and chemical or recombinant preparations. Generally, any biological samples containing biomolecules (e.g., cells, tissue, etc.) may be used. Types of biological samples include, but are not limited to, cells, cell lysate, FFPE (FASP Protein Digestion) digests, tissues including tissue biopsies, whole blood, plasma, serum, urine, stool, saliva, cord blood, chorionic villus samples amniotic fluid, and transcervical lavage fluid. Cell cultures of any of the afore-mentioned biological samples may also be used in accordance with inventive methods, for example, chorionic villus cultures, amniotic fluid and/or amniocyte cultures, blood cell cultures (e.g., lymphocyte cultures), etc. In some embodiments, biological samples comprise diseased cells such cancer or tumor cells. In some embodiments, biological samples are prenatal samples.

Thus, a typical biological sample suitable for the present invention contain heterogeneous biomolecules. In some embodiments, a biological sample contains a mixture of biomolecules from different cell types (e.g., normal cells and diseased cells such as tumor cells). In some embodiments, a biological sample (e.g., blood, serum or plasma) contains a mixture of maternal biomolecules and fetal biomolecules. Suitable samples may be unpurified or minimally purified biological samples or may be made of isolated biomolecules, urine, or plasma/serum.

In some embodiments, the present invention is used to analyze target biomolecules that are present as rare events in a biological sample (also referred to as low abundance biomolecules). In some embodiments, the amount of target biomolecules detected by an inventive method of the present invention represents less than 1% (e.g., less than 0.5%, 0.1%, 0.01%, 0.001%, 0.0001%) of the total biomolecules in a biological sample. In some embodiments, the amount of target biomolecules detected by an inventive method of the present invention represents less than 1 out of a million of the total biomolecules in a biological sample. In some embodiments, the amount of biomolecules detected by an inventive method of the present invention represents less than 1 out of 10 million of the total biomolecules in a biological sample. In some embodiments, the present invention is used to analyze as few as one single copy of a target biomolecule or up to one million or more copies of a target biomolecule.

Detectable Entities

Any of a wide variety of detectable agents can be used in the practice of the present invention. Suitable detectable entities include, but are not limited to: various ligands, radionuclides; fluorescent dyes; chemiluminescent agents (such as, for example, acridinum esters, stabilized dioxetanes, and the like); bioluminescent agents; spectrally resolvable inorganic fluorescent semiconductors nanocrystals (i.e., quantum dots); metal nanoparticles (e.g., gold, silver, copper, platinum, etc.); nanoclusters; paramagnetic metal ions; enzymes; colorimetric labels (such as, for example, dyes, colloidal gold, and the like); biotin; dioxigenin; haptens; and proteins for which antisera or monoclonal antibodies are available.

In some embodiments, the detectable moiety is biotin. Biotin can be bound to avidins (such as streptavidin), which are typically conjugated (directly or indirectly) to other moieties (e.g., fluorescent moieties) that are detectable themselves.

In certain embodiments, a detectable moiety is an enzyme. Examples of suitable enzymes include, but are not limited to, those used in an ELISA, e.g., horseradish peroxidase, beta-galactosidase, luciferase, alkaline phosphatase, etc. Other examples include betaglucuronidase, beta-D-glucosidase, urease, glucose oxidase, etc. An enzyme may be conjugated to a molecule using a linker group such as a carbodiimide, a diisocyanate, a glutaraldehyde, and the like.

A detectable moiety may include more than one chemical entity such as in fluorescent resonance energy transfer (FRET). Resonance transfer results an overall enhancement of the emission intensity. For instance, see Ju et. al. (1995) Proc. Nat'l Acad. Sci. (USA) 92: 4347, the entire contents of which are herein incorporated by reference. A suitable detectable moiety can be an intercalating DNA/RNA dye that have dramatic fluorescent enhancement upon binding to double-stranded DNA/RNA. Examples of suitable dyes include, but are not limited to, SYBR™ and Pico Green (from Molecular Probes, Inc. of Eugene, Oreg.), ethidium bromide, propidium iodide, chromomycin, acridine orange, Hoechst 33258, Toto-1, Yoyo-1, and DAPI (4',6-diamidino-2-phenylindole hydrochloride). Additional discussion regarding the use of intercalation dyes is provided by Zhu et al., Anal. Chem. 66:1941-1948 (1994), which is incorporated by reference in its entirety.

Below are described some non-limiting examples of other detectable moieties.

Fluorescent Dyes

In certain embodiments, a detectable moiety is a fluorescent dye. Numerous known fluorescent dyes of a wide variety of chemical structures and physical characteristics are suitable for use in the practice of the present invention. A fluorescent detectable moiety can be stimulated by a laser with the emitted light captured by a detector. The detector can be a charge-coupled device (CCD) or a confocal microscope, which records its intensity.

Suitable fluorescent dyes include, but are not limited to, fluorescein and fluorescein dyes (e.g., fluorescein isothiocyanine or FITC, naphthofluorescein, 4',5'-dichloro-2',7'-dimethoxyfluorescein, 6-carboxyfluorescein or FAM, etc.), carbocyanine, merocyanine, styryl dyes, oxonol dyes, phycoerythrin, erythrosin, eosin, rhodamine dyes (e.g., carboxytetramethyl-rhodamine or TAMRA, carboxyrhodamine 6G, carboxy-X-rhodamine (ROX), lissamine rhodamine B, rhodamine 6G, rhodamine Green, rhodamine Red, tetramethylrhodamine (TMR), etc.), coumarin and coumarin dyes (e.g., methoxycoumarin, dialkylaminocoumarin, hydroxycoumarin, aminomethylcoumarin (AMCA), etc.), Oregon Green Dyes (e.g., Oregon Green 488, Oregon Green 500, Oregon Green 514, etc.), Texas Red, Texas Red-X, SPECTRUM RED™, SPECTRUM GREEN™, cyanine dyes (e.g., CY-3™, CY-5™, CY-3.5™, CY-5.5™, etc.), ALEXA FLUOR™ dyes (e.g., ALEXA FLUOR™ 350, ALEXA FLUOR™ 488, ALEXA FLUOR™ 532, ALEXA FLUOR™ 546, ALEXA FLUOR™ 568, ALEXA FLUOR™ 594, ALEXA FLUOR™ 633, ALEXA FLUOR™ 660, ALEXA FLUOR™ 680, etc.), BODIPY™ dyes (e.g., BODIPY™ FL, BODIPY™ R6G, BODIPY™ TMR, BODIPY™ TR, BODIPY™ 530/550, BODIPY™ 558/568, BODIPY™ 564/570, BODIPY™ 576/589, BODIPY™ 581/591, BODIPY™ 630/650, BODIPY™ 650/665, etc.), IRDyes (e.g., IRD40, IRD 700, IRD 800, etc.), and the like. For more examples of suitable fluorescent dyes and methods for coupling fluorescent dyes to other chemical entities such as proteins and peptides, see, for example, "The Handbook of Fluorescent Probes and Research Products", $9^{th}$ Ed., Molecular Probes, Inc., Eugene, Oreg. Favorable properties of fluorescent labeling agents include high molar absorption coefficient, high fluorescence quantum yield, and photostability. In some embodiments, labeling fluorophores exhibit absorption and emission wavelengths in the visible (i.e., between 400 and 750 nm) rather than in the ultraviolet range of the spectrum (i.e., lower than 400 nm).

Radioactive Isotopes

In certain embodiments, a detectable moiety is a radioactive isotope. For example, a molecule may be isotopically-labeled (i.e., may contain one or more atoms that have been replaced by an atom having an atomic mass or mass number different from the atomic mass or mass number usually found in nature) or an isotope may be attached to the molecule. Non-limiting examples of isotopes that can be incorporated into molecules include isotopes of hydrogen, carbon, fluorine, phosphorous, copper, gallium, yttrium, technetium, indium, iodine, rhenium, thallium, bismuth, astatine, samarium, and lutetium (i.e. $^{3}H$, $^{13}C$, $^{14}C$, $^{18}F$, $^{19}F$, $^{32}P$, $^{35}S$, $^{64}CU$, $^{67}CU$, $^{67}Ga$, $^{99}mTc$, $^{111}In$, $^{125}I$, $^{123}I$, $^{129}I$, $^{131}I$, $^{135}I$, $^{186}Re$, $^{187}Re$, $^{201}Tl$, $^{212}Bi$, $^{213}Bi$, $^{211}At$, $^{153}Sm$, $^{177}Lu$).

In some embodiments, signal amplification is achieved using labeled dendrimers as the detectable moiety (see, e.g., Physiol Genomics 3:93-99, 2000), the entire contents of which are herein incorporated by reference in their entirety. Fluorescently labeled dendrimers are available from Genisphere (Montvale, N.J.). These may be chemically conjugated to the oligonucleotide primers by methods known in the art.

Detection and Quantification

Various methods can be used to detect, quantify and/or analyze captured target biomolecules. Typically, target biomolecules may be detected through detecting and/or analyzing the binding between the detection reagents and the biomolecule bound to the capture moieties as a result of various bioassays described herein. In some embodiments, target biomolecules may be detected through detecting and/or analyzing signal generated by detectable entity associated with the detection reagents that bound to the captured target biomolecules. In some embodiments, signals emanate from an entity (e.g., a detectable moiety) that is physically associated with a detection reagent at the time the signal is detected. In some embodiments, signals emanate from an entity that is not physically associated with a detection reagent at the time the signal is detected. In some embodiments, the amount of target biomolecule may be determined by quantifying the amount of signals detected relative to a reference or control.

In some embodiments, detectable signals are optical signals, such as, for example, fluorescent or luminescent signals. Various devices may be used to detect a signal associated with a target biomolecule. Typically the signal is an optical signal and an optical detector is used. Optical detectors can include one or more of photodiodes (e.g., avalanche photodiodes), a fiber-optic light guide leading, for example, to a photomultiplier tube, a microscope, and/or a video camera (e.g., a charged couple device (CCD) camera), a flow-through device such as a flow cytometer, or a microarray scanner.

Exemplary methods and apparatus for characterization and quantification of multifunctional objects are discussed in International Patent Application No. PCT/US13/29854 and U.S. Patent Application Publication No. 2013/0244909, the contents of which are incorporated herein by reference in their entireties.

In certain embodiments, signals are converted to numerical values using standard software known in the art. In some embodiments, signals (or numerical values representative of signals) are normalized based on background signals. Any of a variety of software programs known in the art may be used to analyze signals as described herein, including, but not limited to, GENEPIX PRO™ 4.0.1.12 software (Axon Instruments, USA), Feature Extraction (Agilent), Matlab (Mathworks), and the like. Exemplary software program for converting and quantifying signals detected by flow-cytometer from a multifunctional particle as described herein are described in International application PCT/US13/29854, the content of which is incorporated herein by reference.

EXAMPLES

Example 1

Multiplexed Droplet-Assisted Immunoassays

Protein biomarkers are currently the workhorse of molecular diagnostics labs. Multiplexed analysis of many protein markers reduces the labor and costs associated with these tests and increase their predictive power. While existing technologies used for multiplexed immunoassays suffer from inter-target antibody compatibility limitations, we demonstrate the use of substrate-mediated droplet formation with controlled reagent release to overcome these limitations.

Figure 3:
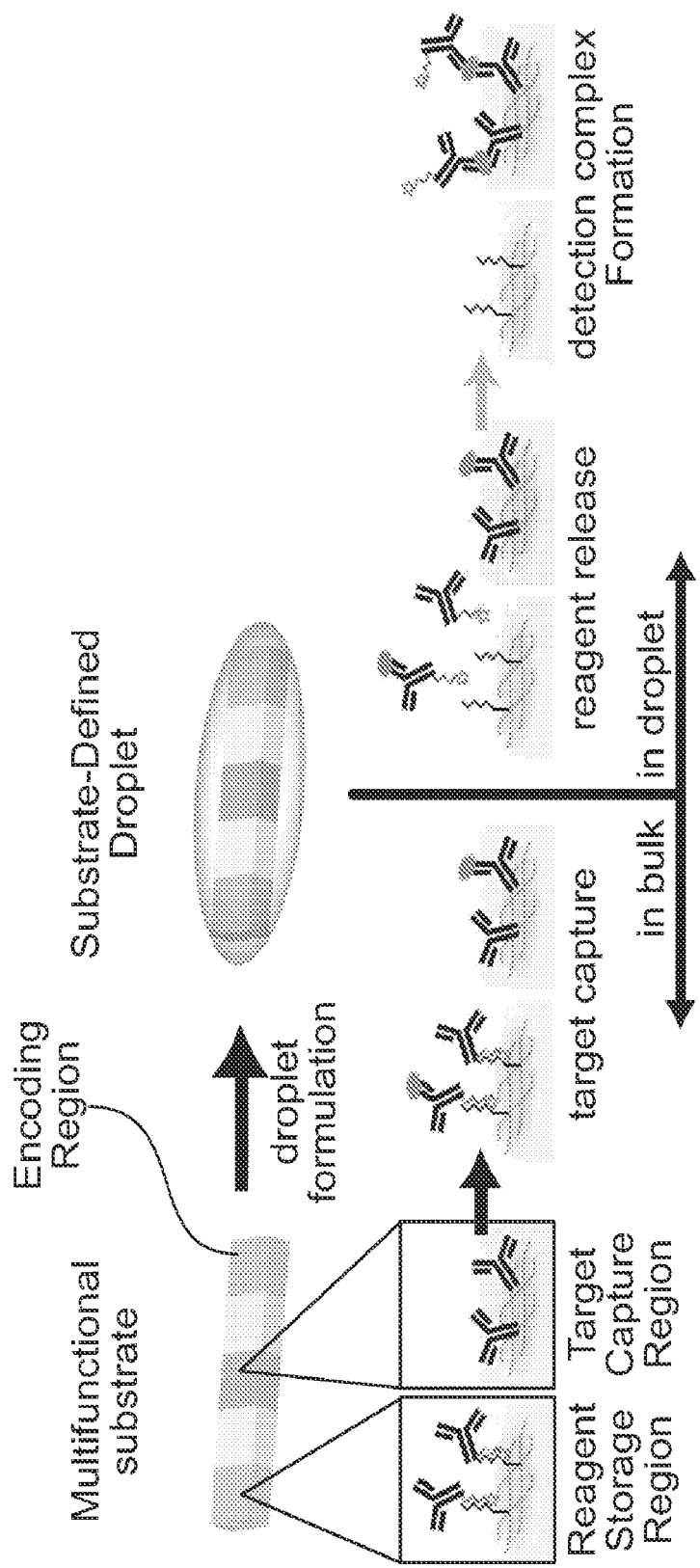
FIG. 3 shows an exemplary droplet-assisted sandwich assay. A multifunctional substrate bears a target capture region decorated with capture antibodies, and a reagent storage region decorated with oligonucleotide anchors that hold oligo-conjugated detection antibodies. After target capture in bulk, an oil phase is introduced to the system, and droplets are created around each substrate. Within the droplet, the detection reagents are released and allowed to form detection complexes in the target capture region of the substrate.

We demonstrate droplet-assisted immunoassays using multifunctional hydrogel microparticles containing Fluorescent Identification Region, a Reagent Storage Region, and a Target Capture Region, as shown in FIG. 3. The Target Capture Region is covalently functionalized with an epitope-specific capture antibody while the Reagent Storage Region is functionalized with an oligonucleotide-modified detection antibody via DNA duplex formation, where a short oligonucleotide tether on the detection antibody is hybridized to the complementary sequence within the Reagent Storage Region. An Encoding Region contains identifying features (e.g., fluorescence signature, graphical barcode, etc.) to identify the substrate.

For droplet-assisted immunoassay, encoded substrates, functionalized with corresponding capture antibodies, detection antibodies, and barcode, are incubated with a biological sample in bulk. During an incubation step, target proteins are specifically captured by the capture antibodies in the Target Capture Region on each particle, and also by the detection antibodies in the Reagent Storage Region. The hydrogel microparticles are then mixed with a fluorinated oil, and the solution is vortexed to form stable, substrate-defined emulsions, ideally with a single particle in each. After isolation, the detection antibody is released from the Reagent Storage Region by increasing the reaction temperature above the melting temperature of the DNA-DNA duplex. After release, the detection antibody is free to migrate to the capture probe region, binding to the captured target protein and enabling fluorescent detection of the captured protein targets. The reaction is then cooled to allow excess detection antibody to be recaptured by the Reagent Storage Region. Target abundance can be determined by relative fluorescent signal via readout on cytometer, fluorescent microscope, etc.

Experimental Overview

In general, the assay includes the following steps:
1. Incubation (in bulk). Capture of specific protein by detection antibodies on encoded hydrogel microparticle substrates.
2. Rinse substrates to remove unbound target [optional, but preferred].
3. Substrate-mediated compartmentalization. Formation of an emulsion, encapsulating each individual particle in a continuous oil phase.
4. Release of detection antibody reagent via temperature increase (in droplets).
5. Binding of Cy5 labeled detection antibody to captured protein target (in droplets).
6. Breaking of emulsion [optional, but preferred].
7. Rinse [optional, but preferred].
8. Scanning of hydrogel particles on a Guava flow cytometer allowing protein target quantitation.

We used hydrogel particles, composed of poly(ethylene glycol), produced via stop-flow lithography (Dendukuri, Gu, Pregibon, Hatton, & Doyle, 2007; Dendukuri, Pregibon, Collins, Hatton, & Doyle, 2006; Pregibon, Toner, & Doyle, 2007). Particles were rod-shaped, each containing a unique capture antibody, detection antibody, and fluorescent code in separate regions along the particle. Capture antibodies were attached using standard EDC chemistry with carboxyl groups in the Target Capture Region of the particles. Oligonucleotide-labeled detection antibodies are reversibly bound within the hydrogel matrix via DNA-DNA duplex formation. Labeled detection antibodies were prepared by Innova Biosciences.

For incubation, we used 35 µl of microparticle suspension is added to each experimental well of a filter plate (Millipore, MSBVN1210), and applied vacuum pressure to remove any liquid, leaving the particles behind in the wells. We then added 50 µL of biological sample on top of the particles, and incubated for 60 minutes at room temperature, with agitation, to allow target proteins to bind to the capture antibodies present on the particles. After target capture the particles are washed twice using filtration to remove non-bound protein.

Following target capture, the particles were re-suspended in 50 µL of low salt buffer and transferred into 0.5 mL PCR tubes. Tubes were vortexed for 15 seconds to disperse the hydrogel particles into the aqueous medium. Immediately following the vortexing, 100 µL of Emulsion Solution, composed of 2% w/w poly(ethylene glycol)-di-(krytox-FSH amide) in FC-40 fluorinated oil, was added to each tube. After addition of the Emulsion Solution, tubes were vortexed vigorously for 30 seconds to produce an emulsion of substrate-defined droplets. The tubes were incubated for 60 minutes at 37° C., releasing the detection antibody for binding with the capture antibody-bound targets.

Following the emulsion step, the reaction was cooled and 25 µL of solvent (1H, 1H, 2H, 2H-Perfluoro-1-Octanol, Sigma) was added to disrupt the emulsion. This mixture was then vortexed for 10 seconds to disperse the solvent throughout the emulsion. The aqueous phase (top) of the tube was then transferred to a filter plate, to separate the particles from the oil phase. The particles were rinsed and each assay well was analyzed on a flow cytometer. Various levels of fluorophore in the coding region(s) are used to determine which particles contain correspond to which protein assay, enabling highly multiplexed protein analysis reactions. Protein targets can be quantified by measuring the amount of fluorescence in the Target Capture region of each hydrogel microparticle.

For flow-based readout, particles were scanned using a Guava easyCyte (6HT or 8HT) flow cytometer. Particles contained a green fluorophore to trigger events in the capture, reagent storage, and encoding regions of each particle. Quantitation of bound target/reagent was accomplished using fluorescence in the RED2 channel, corresponding to Cy5. All post-scan analysis was performed using the Firefly Analysis Workbench software.

Substrate-Mediated Compartmentalization

To determine the efficacy of the particles in defining droplets, hydrogel microparticles were incorporated into an oil-water emulsion. Polyethylene Glycol (PEG) hydrogel microparticles were manufactured via flow lithography in a size of approximately 200 µm by 45 µm by 45 µm, and contained a dye to aid in particle identification. The hydrogel microparticles were suspended in a phosphate buffered saline (PBS) aqueous phase. An Emulsion Solution (2% w/w poly(ethylene glycol)-di-(krytox-FSH amide) in FC-40 fluorinated oil) was then added to the aqueous phase and vortexed vigorously. Various microparticle concentrations, surfactant concentrations and oil to aqueous ratios were tested.

Figure 4:
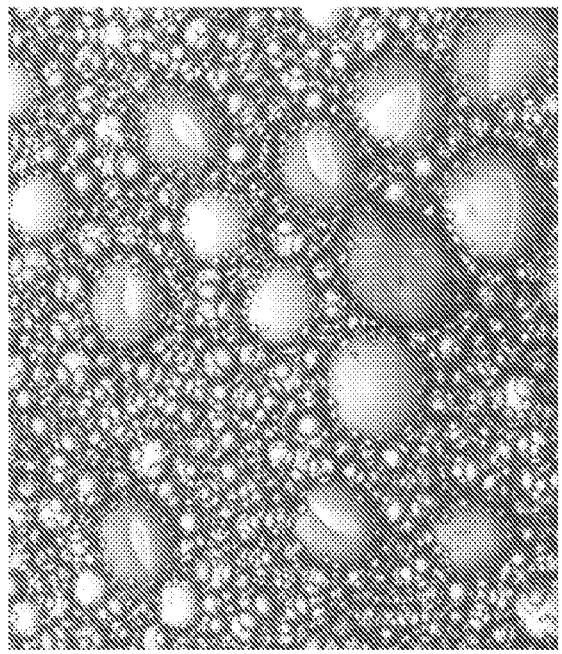
FIG. 4 shows exemplary hydrogel substrate-defined droplets. Rod-shaped particles are shown folded over themselves, due to surface tension, within aqueous droplet compartments.
Figure 4:
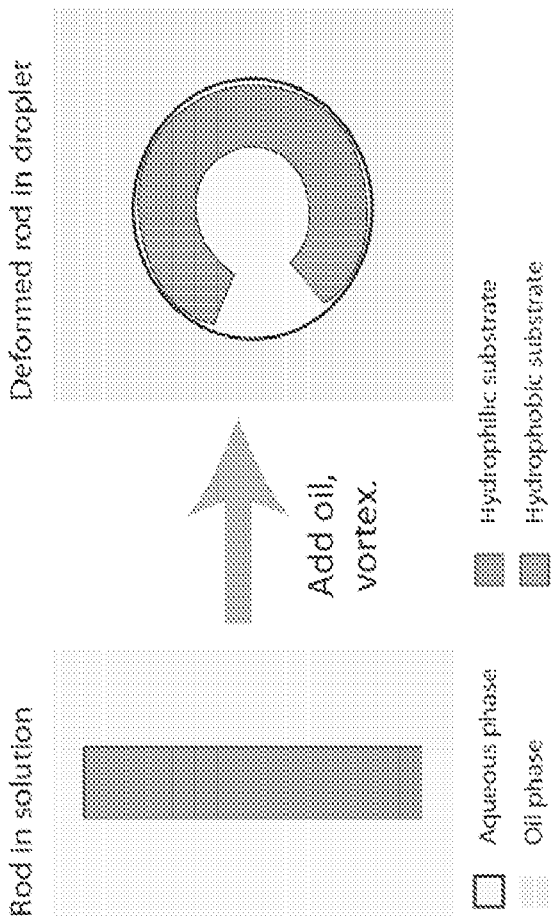

Conditions were optimized to achieve a thermostable emulsion that comprises of a large number of droplets encapsulating a single microparticle. By adjusting the aqueous droplet size to be smaller than the size of a microparticle, single microparticle droplets can be realized. An emulsion prepared with 50 µL of hydrogel microparticles is shown below in FIG. 4. The hydrogel microparticles can be seen to be folding over due to the interfacial forces exerted by the aqueous bubbles trying to minimize their surface area.

Figure 5:
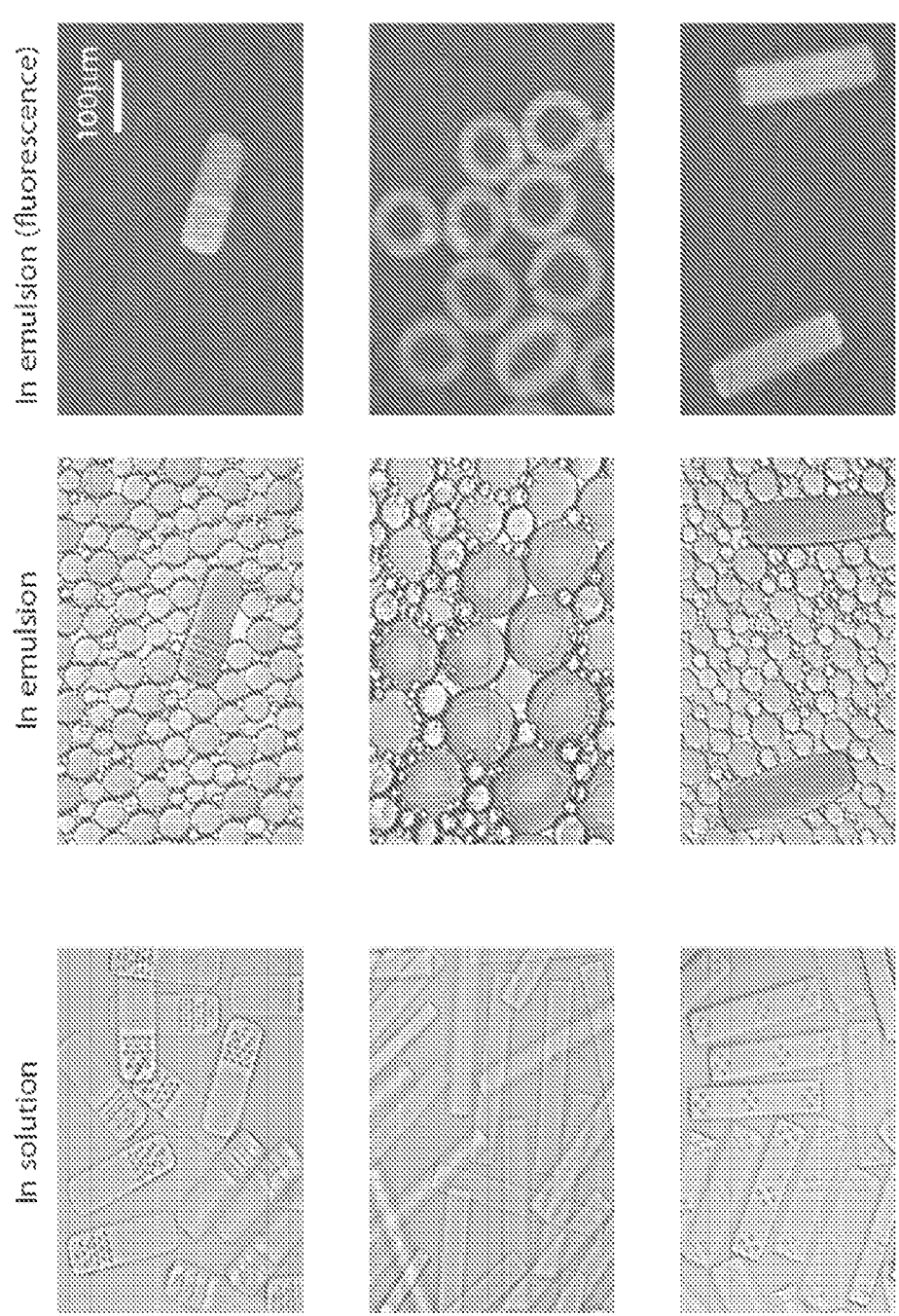
FIG. 5 shows exemplary hydrogel substrate-defined droplets. Shown are particles in solution (left), particles defining aqueous droplets in an emulsion (middle), and particles in droplets imaged under fluorescence (right).

The mechanical properties of the particles used greatly affects the shape of the droplets formed. While rigid particles are less affected by the surface tension of the droplets, flimsy particles can deform significantly when encapsulated. We demonstrate this affect in FIG. 5. Rigid, barcoded particles tend to completely define the shape of the particles. Conversely, long, flexible particles are folded over, taking the shape of the confining droplets. The mechanical properties of the particles can be tuned by altering composition (e.g., material pore size, cross-link density), shape, aspect ratio, etc. Particles can also be made to be reversibly rigid using stimuli like magnetism, electrostatics, etc. For example, flexible paramagnetic particles can be made to stretch in order to align with an external magnetic field (Bong, Chapin, & Doyle, 2010). This phenomenon can be used to break droplets on demand.

Reagent Release

To verify that reagents could be stored and selectively released into the particle-templated reactors, hydrogel microparticles containing a releasable fluorophore were incorporated into an oil-water emulsion. Bi-functional PEG hydrogel microparticles were polymerized containing a bio-inert region and a spatially separated reagent storage region. The reagent storage region contains an oligonucleotide incorporated into the hydrogel matrix via an Acrydite™ anchor on the 5' end of the sequence. A complementary sequence modified with a Cy5 fluorophore was then hybridized onto the oligonucleotide contained in the reagent storage region. The two sequences were designed to have a melting temperature of 37° C. in a low salt phosphate buffer.

Figure 6:
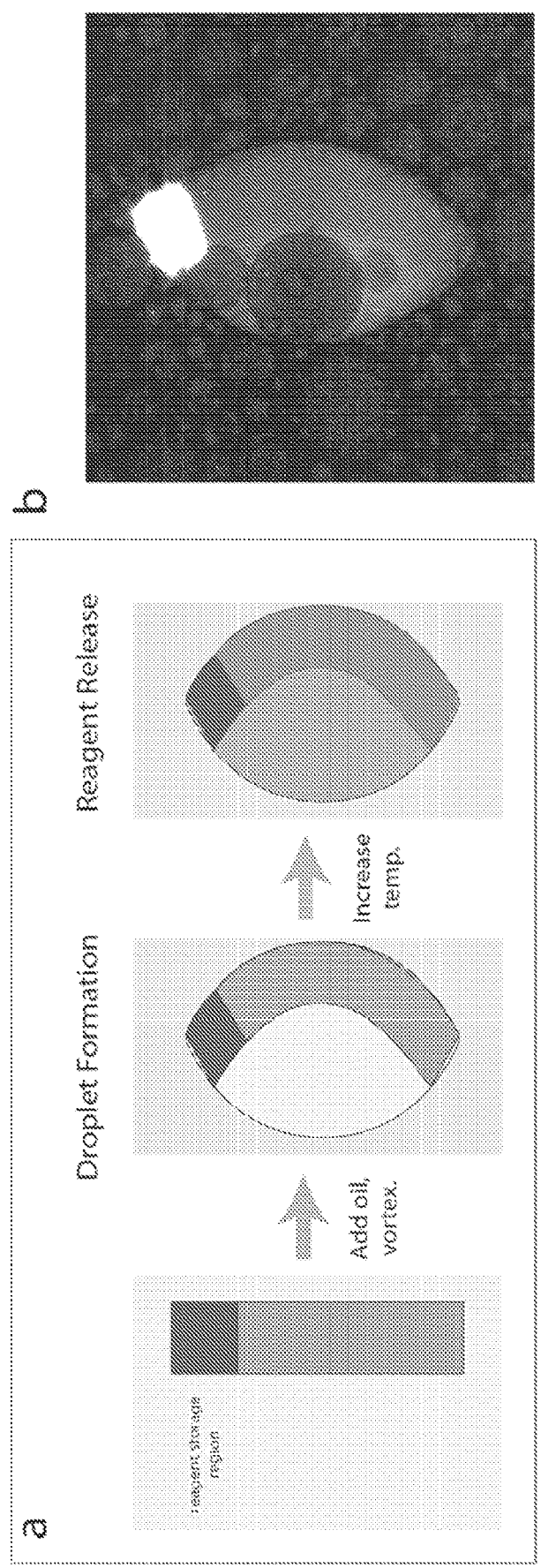
FIG. 6 shows exemplary temperature-controlled release of Cy5-modified oligo from reagent storage region of a multifunctional particle confined within a droplet. Shown are (a) workflow of particle encapsulation and reagent release, and (b) fluorescence image of particle in droplet after release of Cy5-modified oligo.

The hydrogel microparticles containing Cy5-modified oligonucleotide were then re-suspended in a low salt phosphate buffer in PCR tubes. Microparticles were dispersed in the solution via vortexing before an emulsion solution (2% w/w poly(ethylene glycol)-di-(krytox-FSH amide) in fluorinert FC-40) was then added. After addition the two-phase mixture was vortexed until a uniform emulsion was formed. The emulsion was then heated to 37° C. to reach the melting point of the Cy5 containing oligonucleotide. A fraction of the emulsion was then transferred to microscope slide for imaging on an inverted fluorescence microscope. Microparticles were imaged using a metal halide lamp and a 600 nm filter, illuminating the Cy5 dye present in the sample. The resulting image in FIG. 6 shows the boundaries of the droplet illuminated by the released oligonucleotide, confirming reagent can be released and contained into a single droplet. The reagent storage region can also be visualized as the Cy5 oligonucleotides re-hybridize to the anchor as the small volume sample on the microscope slide cools rapidly.

Assay Isolation

To demonstrate the ability to isolate reactions within emulsions, we performed a multiplex assay using reagents that were known to cross-react in bulk. We used multifunctional hydrogel particles with Capture, Reagent Storage, and Encoding regions, functionalized as follows:

Particle #1 (IL-8)
Capture Region: Mouse anti-human IL-8 Ab (R&D Systems, Part 890804)
Reagent Storage Region: oligo-modified Goat anti-human IL-8 Polyclonal Ab (R&D Systems, AF-208-NA)
Encoded Region: Cy3, Intensity Level 1
Particle #2 (anti-goat)
Capture Region: Rabbit Anti-Goat IgG (Sigma, G4018)
Reagent Storage Region: no reagent
Encoded Region: Cy3, Intensity Level 2

For the IL-8 particles, capture antibody was covalently attached to the target capture region using sulfo-NHS chemistry. The attachment was confirmed using an anti-mouse FITC IgG (Sigma, F0257) with readout on an inverted fluorescence microscope. The 11-8 detection antibody was conjugated to a Cy5-labeled oligonucleotide complementary to the anchor present in the reagent storage region of the hydrogel. Oligo-conjugated detection antibodies were hybridized to the reagent storage region of the IL-8 particles in a phosphate buffered saline solution at room temperature for 4 hours. Excess conjugate was then removed from solution using two rinses in the well of a filter plate. The hybridization of the detection antibody oligonucleotide conjugate in the reagent storage region was verified by observing Cy5 fluorescence using a fluorescence microscope.

For the anti-goat particles, the anti-goat antibody was attached to the target capture region using sulfo-NHS chemistry and no reagent was attached to the oligonucleotide anchors present in the reagent storage region of the microparticles. The attachment of the anti-goat antibody was confirmed using anti-rabbit FITC IgG (Sigma, F9887) with imaging on a fluorescence microscope. For identification during analysis, the two particle types (IL-8 and anti-goat) were loaded with distinct levels of Cy3 fluorophore in the encoding region.

To determine the amount of crosstalk between the microparticle types with an without emulsions, the 11-8 and anti-goat microparticles were mixed together in two separate wells. Both wells were then buffer exchanged into a low salt phosphate buffer. One well was then transferred into a PCR tube and vortexed to disperse the particles evenly. Emulsion solution (2% w/w poly(ethylene glycol)-di-(krytox-FSH amide) in fluorinert FC-40) was then added, and the corresponding two phase mixture vortexed until an emulsion was formed. The second well was transferred into a PCR tube and centrifuged to pellet the microparticles, excess volume was then removed down to 10 µL to attempt to mimic the effective concentration in the droplets. Both tubes were then brought to 37° C. to dissociate and release the goat 11-8 detection antibody.

Figure 7:
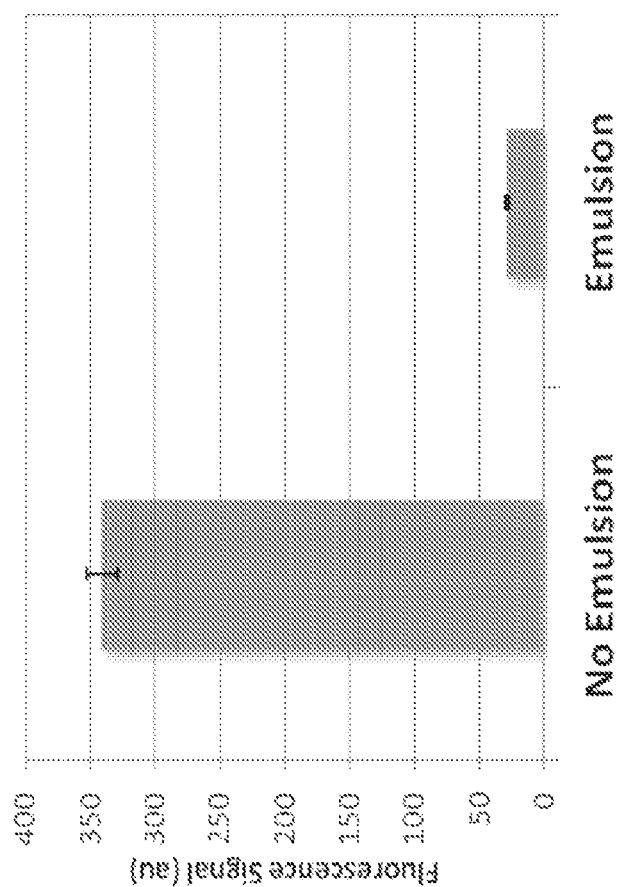
FIG. 7 shows exemplary data demonstrating cross-talk of Cy5-labeled goat anti-human IL-8 antibody released from IL-8 particles on anti-goat particles. When reagent release is performed in isolated droplets, cross-reactivity was dramatically reduced compared to that observed in bulk.

After a one-hour incubation at 37° C. the emulsion was broken by using 25 µl, of solvent (1H, 1H, 2H, 2H-Perfluoro-1-Octanol, Sigma) added to absorb the detergent present in the emulsion solution. This mixture was vortexed for 10 seconds to disperse the solvent. The aqueous phase (top) of the tube was then transferred back to the filter plate in order to separate the particles from remaining oil phase. The second, non-emulsion tube was also transferred back to this same filter plate. The microparticles were then rinsed with phosphate buffer solution and readout on a flow cytometer. The signal measured in the target capture region of the particles of the anti-goat particles are shown in FIG. 7.

Immunoassay Dilution Curve

In order to demonstrate a sandwich assay using substrate-defined droplets and controlled reagent release, we generated a standard curve of IL-8 target. We used the IL-8 particles with a recombinant human 11-8 (R&D Systems, 208-IL), prepared using 10 fold dilutions from 10,000 pg/mL down to 0.1 pg/mL in PBS. Particles were pipetted into 16 wells, followed by sample. Microparticles were incubated with target for 60 minutes at room temperature with agitation. Following target capture, the microparticles were rinsed with phosphate buffered saline to remove unbound target, re-suspended in 50 µl low salt phosphate buffer, and transferred into PCR tubes. Particles were then vortexed and 100 µl of emulsion solution (2% w/w poly (ethylene glycol)-di-(krytox-FSH amide) in Fluorinert FC-40) was added to the tubes. The two phase mixture was then emulsified via vortexing for one minute. After vortexing, the emulsions were placed in a heating block at 37° C. for one hour to allow the detection antibody to dehybridize and interact with the target capture region.

Figure 8:
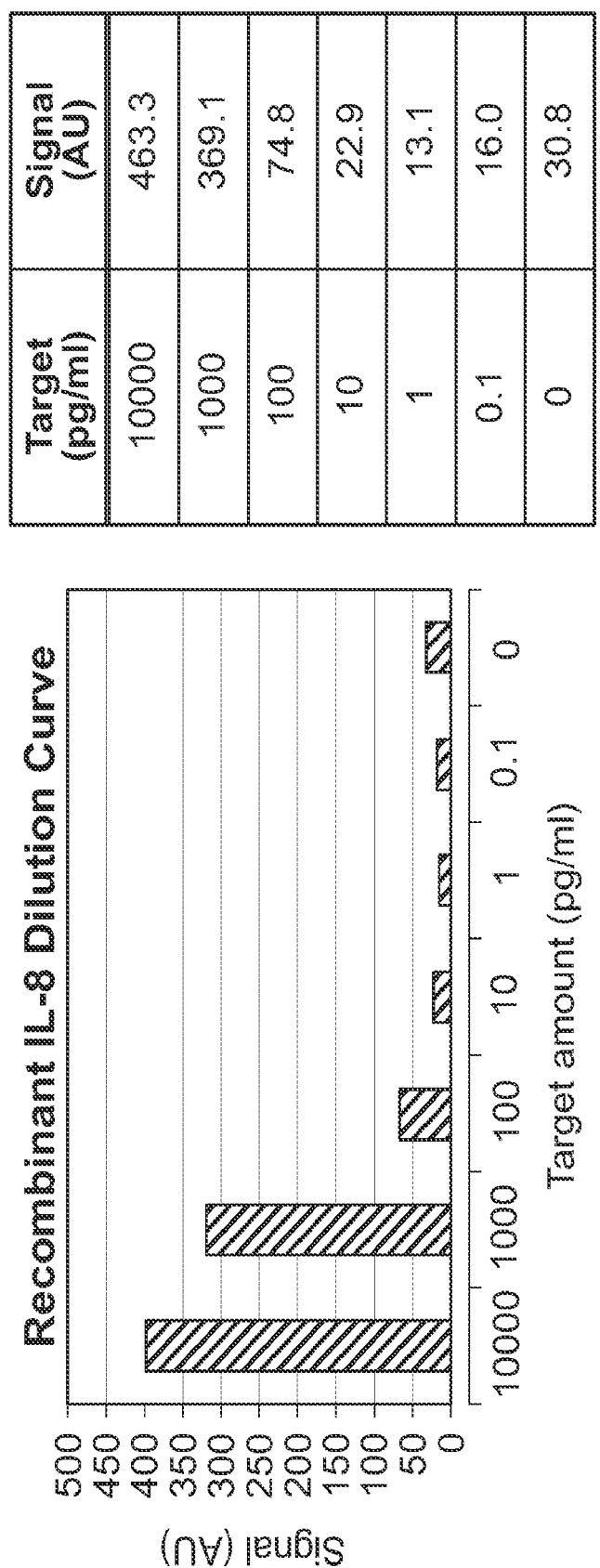
FIG. 8 shows exemplary dilution curve analysis for recombinant human IL-8 using emulsion-isolated reactions.

Following the second incubation, the emulsions were broken through the addition of a solvent (1H, 1H, 2H, 2H-Perfluoro-1-Octanol, Sigma). The tubes were briefly centrifuged to separate the aqueous phase from the oil phase, and the aqueous phase of each tube was then pipetted into the wells of a filter plate for analysis in a flow cytometer. Coefficient of variation was calculated to be 17% measured at the 100 pg/mL titration point. The calculated limit of detection was 41 pg/mL based on background subtracted signal divided by 3× the standard deviation of the negative control. An exemplary dilution curve is shown in FIG. 8.

Example 2

Physical Isolation of Reaction Droplets

Droplet merging or diffusion of biological or chemical agents through the immiscible, continuous oil phase would result in ineffective isolation of individual reactions. A system was designed to assess the degree of droplet merging/coalescence. In order to assess coalescence, hydrogel particles bearing a covalently bound oligonucleotide probe were encapsulated in immiscible oil phase through vigorous vortexing for 30 seconds. A second emulsion was prepared with the aqueous phase consisting of 500 nM reverse complement oligonucleotide to the particle bound probe, labeled with a Cy5 fluorophore. The two emulsions, one containing only naive particles in buffer, the other containing fluorescent oligonucleotide target, were mixed 1:1. The resulting mixed emulsion was incubated for 60 minutes at 37 degrees C. The emulsion was then reversed, and the fluorescent signature on each particle was analyzed using a Guava 8HT flow cytometer to assess particle signal. High signal on many particles would suggest a significant degree of droplet coalescence, resulting in capture of fluorescent complement oligo onto the probe-laden particles.

FIG. 9, parts A, B and C show histograms of the particles resulting from this method, as well as the appropriate controls. Controls used consisted of particles encapsulated in oil with no fluorescent oligonucleotide target present (negative), and particles incubated directly with the fluorescent oligonucleotide without emulsification (positive). The "no encapsulation" particles were expected to show high signal on all particles and, indeed, the mean intensity was found to be 200-300 AFU. The negative control particles were expected to show only background fluorescence, and mean signal was found to be 0-10 AFU. The signal on encapsulated particles mixed with the target fluorescent oligonucleotide was found to be 0-50 AFU for more than 90% of particles. Some fraction of particles was found to have higher fluorescent signal, similar to the level observed of on "no encapsulation" particles. This indicates than some percentage of droplets may be merging/coalescing in this emulsion system. This method can be used to rapidly screen emulsion systems to arrive at optimal conditions that minimizes droplet merging and selects for the most stable conditions.

Example 3

Exemplary Continuous Phase Enabling Two-Phase Reaction Droplet System

An exemplary embodiment of this system is described below. In this system, an aqueous phase containing hydrogel particles is mixed with a continuous immiscible oil phase, resulting in reversible stable encapsulation of individual reactions in the oil phase.

Hydrogel particles consisting of polyethylene glycol and with the dimensions of 100-200 micrometers in the length dimension and 20-100 microns in the width and height directions are used. Particles contain at least one capture antibody within a defined particle region, and at least one detection antibody tethered using complementary oligonucleotides in another region, are added to a biological sample of interest. Each particle type has a specific barcode, or other identifying feature, associated with the target molecule(s) it detects. A plurality of particle types can be used to selectively analyze up to 1000 biological targets simultaneously in a single reaction, with 50-100 of each particle type present in order to provide multiple measurements per target.

For the assay, particles are allowed to mix with the sample for 90 minutes. The particles are then rinsed with PBS buffer and suspended to a volume of 50 microliters. A volume of 150 microliters of oil phase plus surfactant is added to each tube and vortexed vigorously for 30 seconds to create shear forces. The continuous oil phase consists of 4 wt % poly(ethylene glycol)-di-(krytox-FSH amide) in HFE7500 oil. Thirty seconds of vortexing results in droplets that, on average, are much smaller than the hydrogel particles, or contain a single particle. The emulsion is then incubated at 37 degrees C. for 60 minutes, resulting in the release of the detection antibody into the microdroplet reaction compartment and the labeling of bound target captured by the antibody capture moiety. Fifty microliters of disruption solvent (1H, 1H, 2H, 2H-Perfluoro-1-Octanol) is added to the emulsion in order to remove the surfactant and reverse the emulsification. The resulting aqueous phase is filtered through a membrane, and the hydrogel particles washed and suspended in 200 microliters of PBS buffer. The particles can then be analyzed on a fluorescent microscope or plate scanner, and the target signal captured from the initial biological sample can be elucidated based on fluorescent signature intensity.

Example 4

Highly Multiplexed PCR

PCR-based techniques are limited in their ability to multiplex many targets due to high background signals resulting from primer-primer interactions. Technologies such as the ABI TLDA format or the Fluidigm BioMark system utilize microfluidic approaches to physically separate individual reactions in order to prevent many primer combinations from nonspecifically interacting with one another. However, these methods require expensive and complex instrumentation and disposables. Hydrogel microparticles can prepared such that they contain an oligonucleotide probe specific to the nucleic acid target to be analyzed as well as forward and reverse PCR primers reversibly bound within the hydrogel matrix. The microparticles are first mixed with a biological sample of interest, allowing the target to bind to the specific capture probe. Then the particles are suspended in PCR mastermix containing dNTPs, buffers, cations, and polymerase necessary for amplification. After addition of an immiscible oil phase, energy is added to the system and the particles are used to define aqueous compartments for subsequent isolated reactions. During thermocycling, the PCR primers are released into the particle-defined aqueous reactors, allowing for target-specific PCR amplification of the captured nucleic acid target. This amplified product can be recaptured onto the original capture probe within the hydrogel matrix for further manipulation or analysis.

Example 5

Single Cell Analysis

Many cell-based assays utilize the simultaneous lysis and analysis of many cells. The true analytical power of these methods is limited as the results reflect the average of the cell population, not the true characteristics of the individual cells. The ability to analyze individual cells one at a time will mitigate this shortcoming. Hydrogel microparticles containing cell-specific antibodies can be mixed with a cell population such that, on average, one cell binds to each hydrogel particle. The particles can then be encapsulated in a continuous immiscible oil phase, resulting in hydrogel microparticle defined compartments that contain, on average, one cell per compartment. The cells can then be lysed and their contents analyzed by studying the binding of specific analytes to capture moieties contained within the hydrogel particle matrix. In this manner, many multi-analyte single-cell studies can be carried out in hydrogel-templated microreactors at the same time. This will increase the power and availability of single-cell analysis techniques. Alternatively, the particles may bear holes or cavities in which individual cells can rest, or particles may be polymerized around cells, encapsulating them in a hydrogel matrix.

Example 6

Digital PCR in Particle-Defined Microreactors

Droplet-digital PCR, commercialized on droplet platforms such as Bio-Rad QuantaLife and RainDance, allows for absolute quantitation of nucleic acid targets. These systems rely on the production of many highly uniform droplets containing PCR primers. These droplets are merged with a limited dilution of a biological sample such that droplets will contain no more than 1 nucleic acid target molecule on average, and qPCR is carried out with resulting in a measurable fluorescent for each target molecule. Rather than relying on expensive fluidic systems to produce monodisperse droplets, hydrogel microparticles can be used. Monodisperse particles, typically between 1 µm and 100 µm in diameter, are mixed with the PCR master mix containing a limiting dilution of the biological sample, dNTPs, PCR primers, appropriate buffer conditions, and polymerase enzyme. Hydrogel microparticles are then dispersed in an immiscible continuous oil phase, resulting in monodisperse aqueous microreactors that contain, on average, one template molecule. After thermocycling with a fluorescently labeled primer, the amplified product is captured on an oligonucleotide capture probe within the hydrogel matrix. These particles can then be analyzed using an instrument such as a flow cytometer to give a true quantitative measurement of specific nucleic acid molecules in a given sample.

Example 7

Cell Secretion Analysis

Exosomes, cytokines, and other biological entities are released by cells. It has been postulated that these secretions may facilitate, among other things, cell-to-cell communication. These extracellular molecules may be difficult to analyze at the level of a single cell. By encapsulating or capturing one or several cells with a multifunctional hydrogel particle, it is possible to obtain additional insights into cell secretions or cell-cell signaling molecules. Hydrogel microparticles containing cell-specific capture moieties are mixed with cell population such that, on average, one cell is captured per hydrogel substrate. The hydrogel microparticles are then dispersed in an immiscible continuous oil phase, resulting in aqueous compartments that contain, on average, one cell. The biomolecules released by intact single cells can be captured and analyzed using defined regions within the microparticle substrates that contain protein, antibody, or oligonucleotide probes. These molecules, typically in extremely low abundance, can be quantified in the picoliter-scale reactors defined by the hydrogel microparticle substrates as the local concentration of these markers will be very high.

Example 8

Multiplexed ChIP-Seq

Chromatin-immunoprecipitation has emerged as an invaluable tool for investigating the interaction between DNA and DNA-binding proteins such as transcription factors, nucleosomes, and other complexes. These procedures typically utilize an individual antibody to pull down DNA-chromatin complexes, followed by sequencing or PCR to characterize the DNA fragments. Many hydrogel microparticles, each containing a distinct capture antibody can be used examine many more DNA-protein complexes in the same sample at the same time. Microparticles are encapsulated in a continuous oil phase, following the specific binding of the DNA-protein complex to each particle. Then an antibody-specific DNA tag is released in into the aqueous compartment via a controlled stimulus such as heat. A blunt end or sticky end ligase, combined with the appropriate end-repair conditions, can be used to ligate the DNA tag onto each captured DNA fragment. These adapted DNA fragments can be purified and analyzed with sequencing or PCR such that the identity of each antibody-protein complex can be elucidated based on the known oligonucleotide tag ligated to the DNA fragment. This enables highly multiplexed ChIP reactions in the same well.

Other Embodiments and Equivalents

While the present disclosures have been described in conjunction with various embodiments and examples, it is not intended that they be limited to such embodiments or examples. On the contrary, the disclosures encompass various alternatives, modifications, and equivalents, as will be appreciated by those of skill in the art. Accordingly, the descriptions, methods and diagrams of should not be read as limited to the described order of elements unless stated to that effect.

Although this disclosure has described and illustrated certain embodiments, it is to be understood that the disclosure is not restricted to those particular embodiments. Rather, the disclosure includes all embodiments that are functional and/or equivalents of the specific embodiments and features that have been described and illustrated.

The present specification incorporates herein by reference in their entireties U.S. Pat. No. 7,947,487, titled "Multifunctional Encoded Particles for High-Throughput Analysis," issued May 24, 2011; U.S. Patent Application Publication No. 2010/0172898, titled "Microstructure Synthesis by Flow Lithography and Polymerization," filed Mar. 15, 2010; and U.S. Patent Application Publication No. 2013/0210653, titled "Scanning Multifunctional Particles," filed Feb. 7, 2013.

We claim:

1. A method for analyzing biomolecules, comprising:
   a) incubating a sample with a plurality of multifunctional substrates, wherein each multifunctional substrate comprises a target capture region bearing one or more capture moieties, each of which specifically binds a target biomolecule, and a reagent storage region bearing one or more detection reagents through a releasable means, under conditions that permit binding between the target biomolecule and the capture moieties;
   b) contacting an immiscible fluid with the plurality of multifunctional substrates in a carrier fluid, thereby forming a plurality of compartments, each comprising an individual multifunctional substrate, and wherein the shape of each compartment is substantially defined by the shape of the multifunctional substrate;
   c) releasing the one or more detection reagents from the reagent storage region such that the detection reagents bind to the target biomolecule bound to the capture moieties within an individual compartment; and
   d) analyzing the binding between the detection reagents and the biomolecule bound to the capture moieties, thereby analyzing the presence or amount of the target biomolecule in the sample.

2. The method of claim 1, wherein the multifunctional substrates are multifunctional microparticles.

3. The method of claim 1, wherein the multifunctional substrates are made of hydro gel.

4. The method of any claim 2, wherein the microparticles are non-spherical particles.

5. The method of claim 1, wherein the plurality of multifunctional substrates comprise polydisperse microparticles between 1 µm and 500 µm in their longest dimension.

6. The method of claim 1, wherein the one or more capture moieties are selected from antibodies, nanobodies, oligonucleotide probes, peptide nucleic acids, small molecules, aptamers, cells, bacteria, viruses, organelles, peptides, or combination thereof.

7. The method of claim 1, wherein the one or more detection reagents are selected from detection antibodies, nano bodies, enzymes, PCR primers, proteins, oligonucleotides, peptides, aptamers, small molecules, other chemical compounds, or combination thereof.

8. The method of claim 7, wherein the one or more detection reagents are labeled with a detection moiety selected from fluorophores, chromophores, radioisotopes, biotin, enzyme products, antibodies, quantum dots, molecular beacons, and/or aptamers.

9. The method of claim 1, wherein the multifunctional substrates comprise one or more hydrophobic regions.

10. The method of claim 1, wherein the immiscible fluid is an oil and the carrier fluid is an aqueous fluid.

11. The method of claim 1, wherein the immiscible fluid is an aqueous fluid and the carrier fluid is an oil.

12. The method of claim 1, wherein the target biomolecule is a protein, a nucleic acid, a cell, a bacteria, or a chemical compound.

13. The method of claim 1, wherein the releasable means are selected from reversible interactions, an irreversible reaction, reversible crosslinkers, or photocleavable linkers.

14. The method of claim 13, wherein the reversible interactions are selected from electrostatic interactions, physical interactions, magnetic interactions, chemical interactions, or nucleic acid duplex formation.

15. The method of claim 1, wherein the one or more detection reagents are released from the reagent storage region into the compartment in a controlled manner.

16. The method of claim 15, wherein the controlled manner comprises using heat, ultraviolet light, visible light, microwave radiation, enzymatic catalysis, pH, or a specific chemical agent as a stimulus.

17. The method of claim 1, wherein the contacting step comprises a step of emulsification.

18. The method of claim 1, wherein the each multifunctional substrate further comprises an encoding region.

19. The method of claim 1, wherein the multifunctional substrates are analyzed with a flow cytometer or microarray scanner based on a fluorescent or visible identifier.

* * * * *